US006842638B1

(12) United States Patent
Suri et al.

(10) Patent No.: US 6,842,638 B1
(45) Date of Patent: Jan. 11, 2005

(54) ANGIOGRAPHY METHOD AND APPARATUS

(75) Inventors: Jasjit S. Suri, Highland Heights, OH (US); Kecheng Liu, Solon, OH (US); Dee H. Wu, Shaker Heights, OH (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 412 days.

(21) Appl. No.: 10/010,773

(22) Filed: Nov. 13, 2001

(51) Int. Cl.$^7$ ............................................... A61B 5/05
(52) U.S. Cl. .................... 600/425; 600/431; 600/420; 382/128; 382/130; 382/131
(58) Field of Search ................................ 600/407, 425, 600/427, 410–411, 416, 420, 431; 382/190, 199, 128, 130, 131–132, 266–269; 128/920, 922–923

(56) References Cited

U.S. PATENT DOCUMENTS

| | | | |
|---|---|---|---|
| 5,570,404 A | 10/1996 | Liang et al. .................... 378/8 |
| 5,699,799 A | 12/1997 | Xu et al. ................. 128/653.1 |
| 5,768,405 A * | 6/1998 | Makram-Ebeid ............ 382/128 |
| 5,832,134 A | 11/1998 | Avinash et al. ............. 382/257 |
| 6,058,218 A | 5/2000 | Cline ......................... 382/254 |
| 6,073,042 A | 6/2000 | Simonetti ................... 600/420 |
| 6,366,800 B1 * | 4/2002 | Vining et al. ............... 600/425 |
| 6,385,332 B1 * | 5/2002 | Zahalka et al. ............. 382/128 |
| 6,690,816 B2 * | 2/2004 | Aylward et al. ............ 382/128 |
| 2002/0136440 A1 * | 9/2002 | Yim et al. ................... 382/131 |
| 2003/0031351 A1 * | 2/2003 | Yim ........................... 382/130 |
| 2003/0076987 A1 * | 4/2003 | Wilson et al. .............. 382/128 |

OTHER PUBLICATIONS

Stein, et al. "Tracing of Thin Tubular Structures in Computer Tomographic Data", Computer Aided Surgery 3:83–88 (1998).

Sato, et al., "Three–Dimensional Multi–Scale Line Filter For Segmentation and Visualization of Curvilinear Structures in Medical Images", Medical Image Analysis (1998) V. 2, N. 2, pp 143–168.

Anderson, et al., "Artifacts in Maximum–Intensity–Projection Display of MR Angiograms", AJR 154:623–629 Mar. 1990.

Suri, et al., "Shape Recovery Algorithms Using Level Sets in 2–D/3–D Medical Imagery: A State–of–the–Art Review", IEEE Trans. On Information Technology in Biomedicine, V. 6, N. 1, Mar. 2002.

Suri, "2–D Fast MR Brain Segmentation", Int'l Journal of Engineering in Medicine & Biology (EMBS) V. 20, N. 4, pp. 84–95, Jul./Aug. 2001.

Suri, "White Matter/Gray Matter Boundary Segmentation Using Geometric Snakes: A Fuzzy Deformable Model", Singh, et al. (Eds.): ICAPR 2001, LNCS 2013, pp. 331–338, 2001.

Wust, et al., "Evaluation of Segmentation Algorithms For Generation of Patient Models in Radiofrequency Hyperthermia", Phys. Med. Biol. 43 (1998) 3295–3307.

\* cited by examiner

*Primary Examiner*—Eleni Mantis Mercader
(74) *Attorney, Agent, or Firm*—Fay, Sharpe, Fagan, Minnich & McKee, LLP

(57) ABSTRACT

A two-dimensional slice formed of pixels (376) is extracted from the angiographic image (76) after enhancing the vessel edges by second order spatial differentiation (78). Imaged vascular structures in the slice are located (388) and flood-filled (384). The edges of the filled regions are iteratively eroded to identify vessel centers (402). The extracting, locating, flood-filling, and eroding is repeated (408) for a plurality of slices to generate a plurality of vessel centers (84) that are representative of the vascular system. A vessel center (88) is selected, and a corresponding vessel direction (92) and orthogonal plane (94) are found. The vessel boundaries (710) in the orthogonal plane (94) are identified by iteratively propagating (704) a closed geometric contour arranged about the vessel center (88). The selecting, finding, and estimating are repeated for the plurality of vessel centers (84). The estimated vessel boundaries (710) are interpolated (770) to form a vascular tree (780).

28 Claims, 29 Drawing Sheets

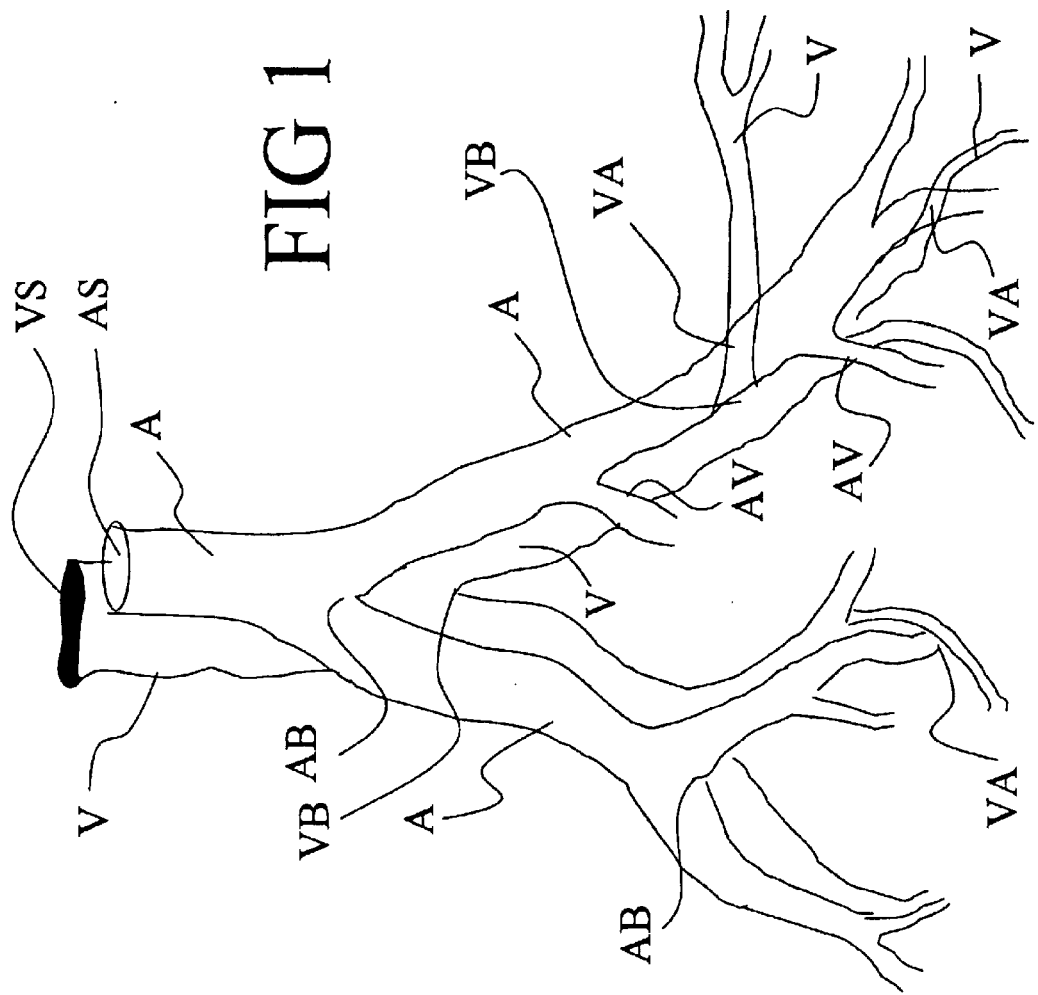

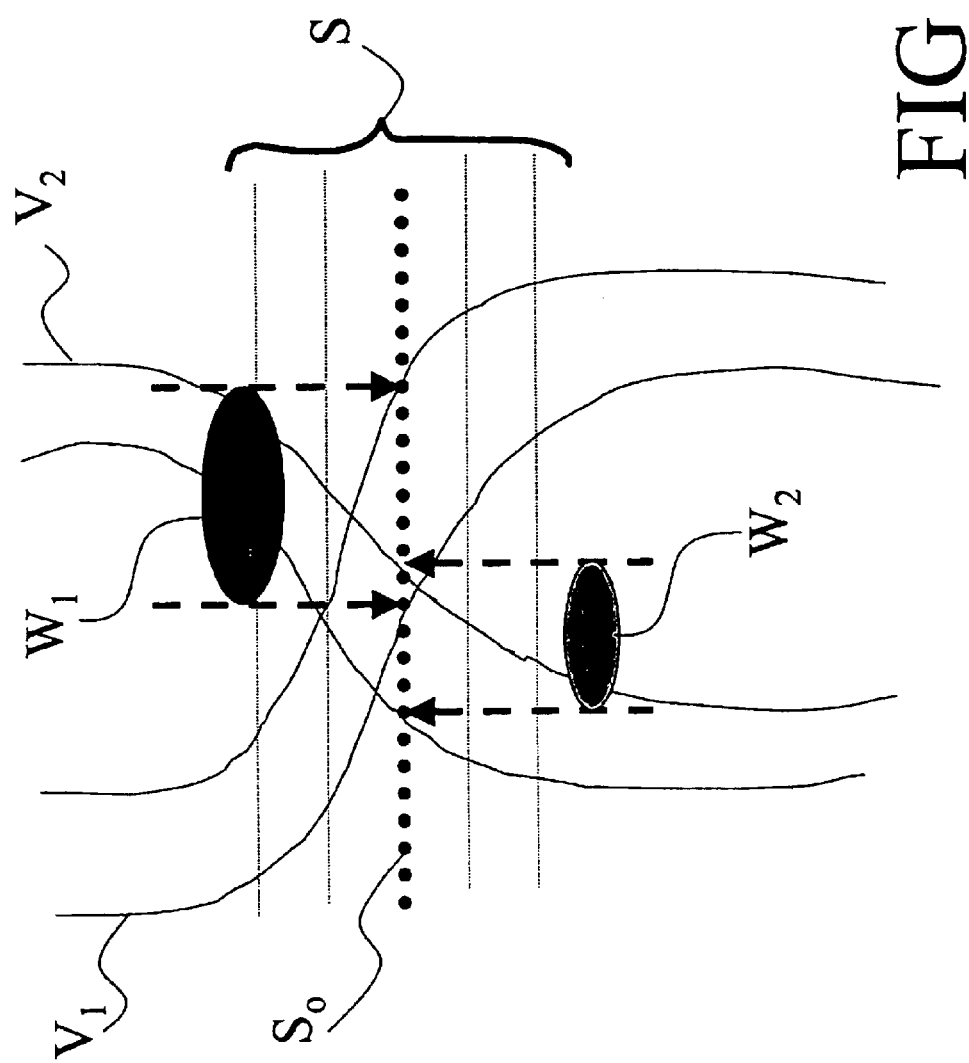

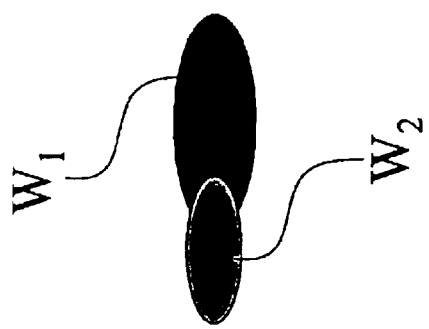
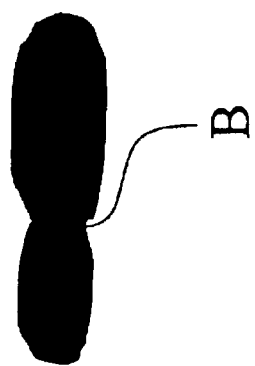
FIG 3A
FIG 3B

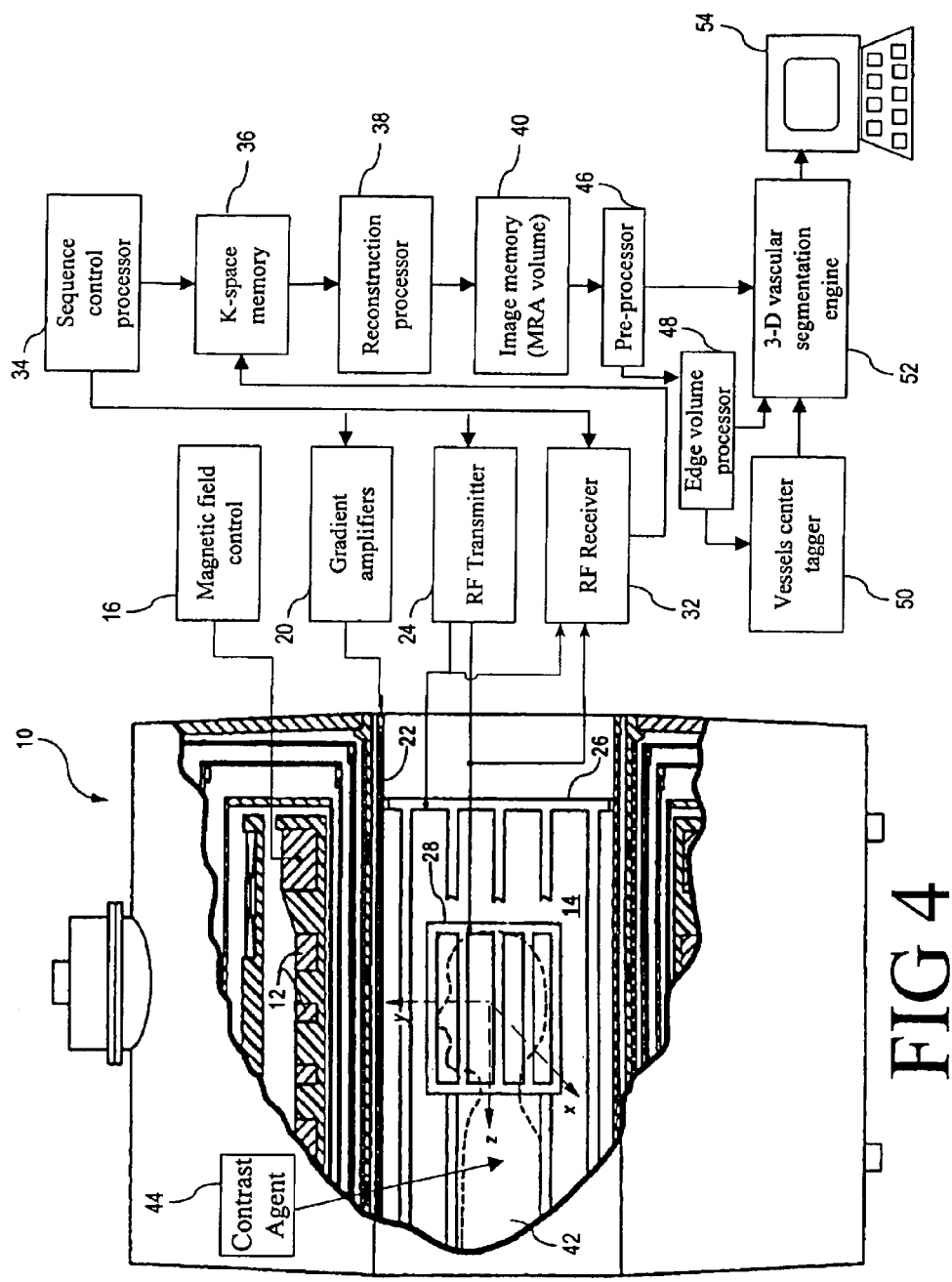

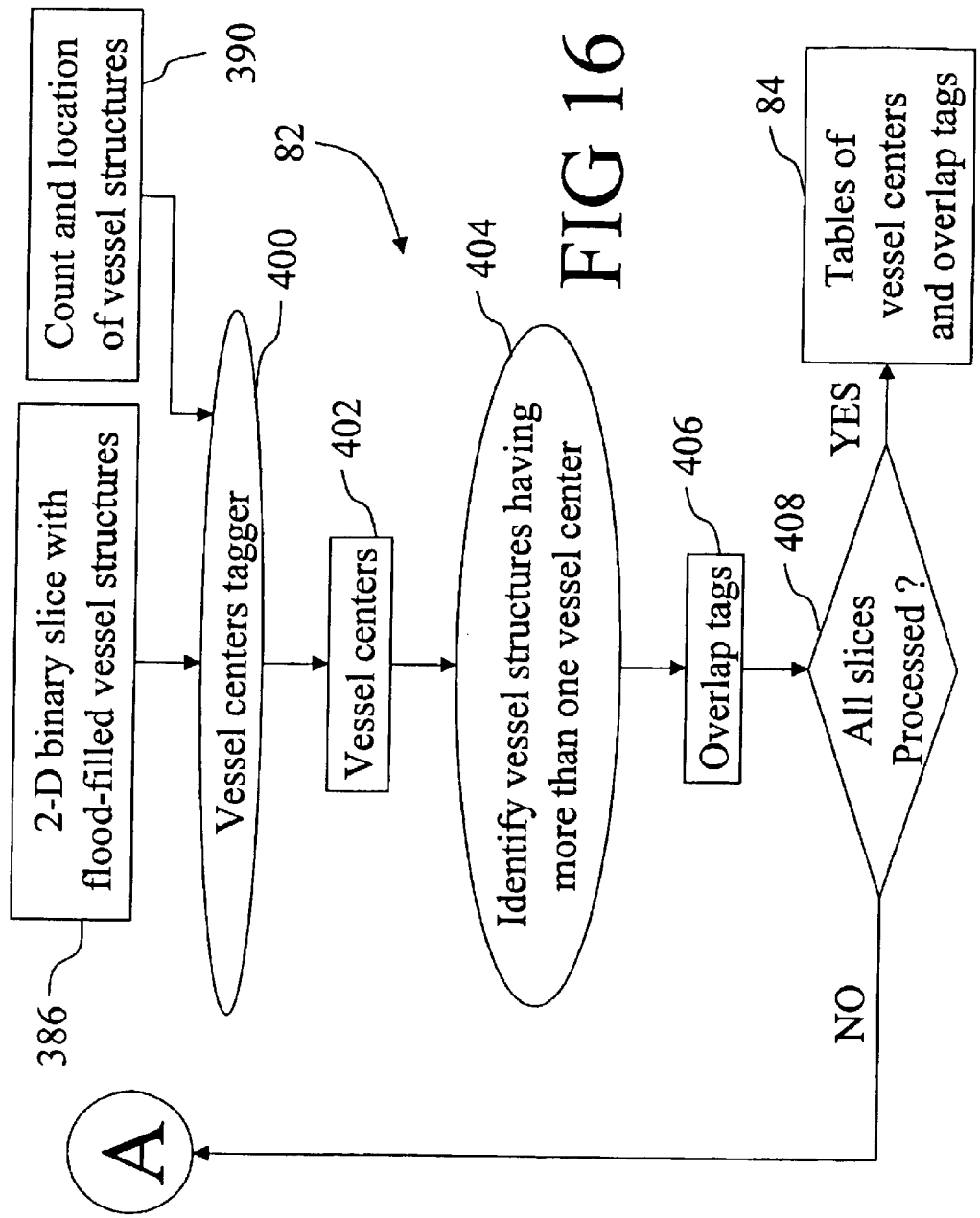

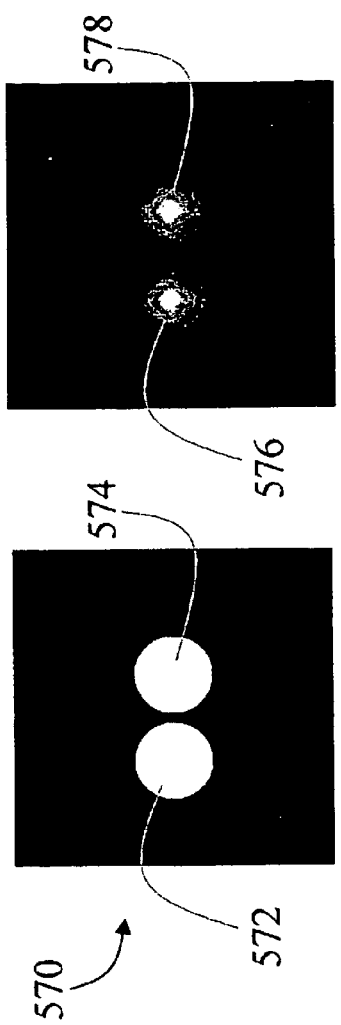
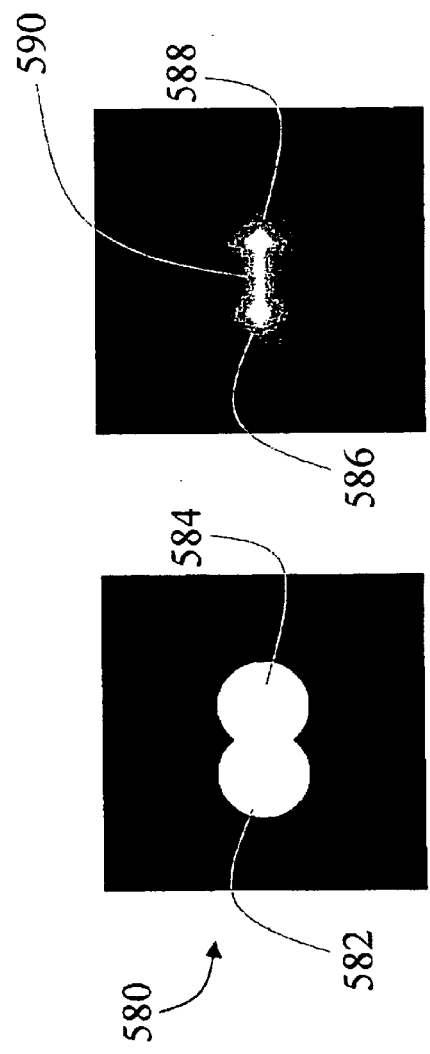
FIG 22A
FIG 22B
FIG 22C
FIG 22D

ANGIOGRAPHY METHOD AND APPARATUS

BACKGROUND OF THE INVENTION

The present invention relates to the medical imaging arts. It particularly relates to angiography using the magnetic resonance imaging (MRI) and computed tomography (CT) medical imaging techniques, and will be described with particular reference thereto. However, the invention will also find application in conjunction with other three-dimensional imaging modalities as well as in other imaging arts in which thin structures or networks with overlapping or furcated portions are advantageously differentiated from extraneous imaged structures and background noise or tracked in three dimensions.

Catastrophic medical events such as heart attacks and strokes that result from underlying vascular problems are a leading cause of death in the United States. Plaque buildup on the inside of the vascular walls can lead to strokes, coronary heart disease, and other medical conditions such as vessel rupture. Many Americans suffer from chronic vascular diseases which degrade quality of life.

Angiography relates to the imaging of blood vessels and blood vessel systems, and as such is a powerful medical diagnostic for identifying and tracking vascular diseases. Angiography enables improved surgical planning and treatment, improved diagnosis and convenient non-invasive monitoring of chronic vascular diseases, and can provide an early indication of potentially fatal conditions such as aneurysms and blood clots. The ability of certain types of angiography to accurately characterize the vessel lumen is particularly valuable for diagnosing plaque buildup on the vessel walls.

Angiography is performed using a number of different medical imaging modalities, including biplane X-ray/DSA, magnetic resonance (MR), computed tomography (CT), ultrasound, and various combinations of these techniques. Two-dimensional or three-dimensional angiographic data can be acquired depending upon the medical imaging modality and the selected operating parameters. Certain types of angiography employ invasive contrast enhanced methodologies in which a contrast agent that accentuates the vascular image contrast is administered to the patient prior to the imaging session. Some angiography techniques, such as MR imaging, are also capable of providing vascular contrast using non-invasive methodologies that take advantage of intrinsic aspects of the vascular system, such as the blood motion or flow, to enhance the vascular contrast without employing an administered contrast agent. For either contrast-enhanced or non-contrast-enhanced angiography, the vasculature imaging is effectuated by either a signal enhancement in the vascular regions (white blood angiography), or by a signal suppression in the vascular regions (black blood angiography).

The analysis of angiographic images by medical personnel is often hindered by image imperfections or intervening non-vascular structures (e.g., bone, organs, and the like). Even in the absence of such problems, however, the sheer complexity of the vascular system and its myriad subsystems severely complicates image interpretation.

With reference to FIG. 1, a schematic portion of an exemplary vasculature is shown, including an arterial sub-system A and a venous sub-system V. As is often the actual situation in the human body, the two sub-systems A, V are shown in FIG. 1 arranged in a substantially parallel manner. Furthermore, there are numerous points where, in the view shown, an artery portion overlaps a vein portion: exemplary points are designated AV. Similarly, there are numerous points where the a vein portion overlaps an artery portion: exemplary points are designated VA. Another complexity arises at furcation points. FIG. 1 shows exemplary artery bifurcations AB and exemplary vein bifurcations VB.

With reference to FIG. 2, an exemplary vascular crossing is shown, in which a vessel $V_1$ and a vessel $V_2$ cross. In three-dimensional angiography, the image is typically created by imaging a plurality of parallel planes S which are then combined to form a three-dimensional image representation. For an exemplary slice $S_o$ oriented perpendicular to the vessels $V_1$ and $V_2$, the image of the vessel $V_1$ in the plane $S_o$ is shown superimposed as $W_1$. Similarly the image of the vessel $V_2$ in the plane $S_o$ is shown superimposed as $W_2$.

With reference to FIG. 3A, it is seen that the vessel images $W_1$ and $W_2$ are overlapping in the image slice $S_o$. FIG. 3B shows the overlapping vessel images $W_1$ and $W_2$ as they would appear in a typical angiographic image. Since the contrast is essentially identical for $W_1$ and $W_2$, it will not be clear to medical personnel whether the overlapping vessels represent crossing arteries, crossing veins, an artery crossing a vein, a vein crossing an artery, a vein bifurcation point, an artery bifurcation point, a closely positioned but non-overlapping pair of vessels, et cetera.

The vascular complexity issues described with reference to FIGS. 1 through 3B are advantageously addressed by automated vascular segmentation systems. These systems differentiate the vasculature from non-vascular structures, background levels, imaging system artifacts such as noise, and the like. Many segmentation engines employ tracking systems which track a vessel starting from an initial seed location. Tracking systems can track the vessel skeleton while simultaneously quantifying the vessel lumen, and such systems are particularly useful for accommodating the varying vessel diameters usually encountered in following a blood vessel. Tracking systems also can separate out individual vessel branches. In the exemplary FIG. 1, a tracking system starting at artery seed AS will track the arterial branch A, while the tracking system starting at vein seed VS will track the venous branch V. In this manner, artery-vein separation is achievable.

However, tracking methods of the prior art have numerous disadvantages, principally due to the localized nature of the tracking analysis. Tracking can be cumbersome and inaccurate, particularly in areas of very high vascular densities such as in the brain. Bifurcation points, tortuous or occluded vessels, vessel overlaps, intertwined vessels, partial volume averaging and other imaging artifacts, and vessel gaps can act alone or in various combinations to produce localized disjoints of the vascular path (or localized disjoints of the angiographic image of the vascular path) which prevent successful vessel tracking. Furthermore, at vessel overlaps the wrong vascular system may be tracked. For example, a tracking system following the arterial branch A of FIG. 1 could fail and begin tracking the venous branch V at any of the crossing points AV, VA.

The present invention contemplates an improved angiographic method and apparatus which overcomes the aforementioned limitations and others.

SUMMARY OF THE INVENTION

According to one aspect of the invention, an apparatus is disclosed for producing an angiographic image representation of a subject. An imaging scanner acquires imaging data from at least a portion of a subject. The imaging data includes vascular contrast. A reconstruction processor reconstructs an image representation from the imaging data. The image representation is formed of image elements and exhibits vascular contrast. A processor converts the image representation into an edge-enhanced image representation having enhanced vascular edges and divides the edge-enhanced image representation into at least one two-dimensional slice formed of pixels. For each slice, the processor flood-fills the vascular edges to form filled regions defined by pixels having a first value, identifies vessel centers through iterative removal of pixels having the first value from around the edges of the filled regions, and segments, tracks, extracts, enhances, or identifies vascular information contained in the angiographic image using the identified vessel centers as operative inputs.

According to another aspect of the invention, a method is disclosed for characterizing a vascular system in a three-dimensional angiographic image comprised of voxels. A two-dimensional slice formed of pixels is extracted from the angiographic image. Imaged vascular structures are located in the slice. The imaged vascular structures are flood-filled to form filled regions defined by pixels having a first value. The edges of the filled regions are iteratively eroded to identify vessel center points. The extracting, locating, flood-filling, and eroding are repeated for a plurality of slices to generate a plurality of vessel center points that are representative of the vascular system.

According to another aspect of the invention, a method is disclosed for tracking a vascular system in an angiographic image. A plurality of vessel centers are identified in three dimensions that are representative of the vascular system. A first vessel center is selected. A first vessel direction is found corresponding to the local direction of the vessel at the first vessel center. A first slice is defined that is orthogonal to the first vessel direction and includes the first vessel center. Vessel boundaries are estimated in the first slice by iteratively propagating a closed geometric contour arranged about the first vessel center. The selecting, finding, defining, and estimating are repeated for the plurality of vessel centers. The estimated vessel boundaries are interpolated to form a vascular tree.

According to yet another aspect of the invention, an apparatus for characterizing a vascular system in a three-dimensional angiographic image comprised of voxels is disclosed. A means is provided for extracting from the angiographic image a two-dimensional slice formed of pixels. A means is provided for locating imaged vascular structures in the slice. A means is provided for flood-filling the imaged vascular structures to form filled regions defined by pixels having a first value. A means is provided for iteratively eroding the edges of the filled regions to identify vessel center points. A means is provided for generating a plurality of vessel center points that are representative of the vascular system. The means for generating is in operative communication with the means for extracting, the means for locating, the means for flood-filling, and the means for eroding.

According to still yet another aspect of the invention, an apparatus for tracking a vascular system in an angiographic image is disclosed. A means is provided for identifying a plurality of vessel centers in three dimensions that are representative of the vascular system. A means is provided for selecting a first vessel center. A means is provided for finding a first vessel direction corresponding to the local direction of the vessel at the first vessel center. A means is provided for defining a first slice that is orthogonal to the first vessel direction and includes the first vessel center. A means is provided for estimating vessel boundaries in the first slice by iteratively propagating a closed geometric contour arranged about the first vessel center. A means is provided for interpolating the estimated vessel boundaries to form a vascular tree after the selecting, finding, defining, and estimating have been repeated for the plurality of vessel centers.

One advantage of the present invention is that it is a global technique which overcomes segmentation failures often encountered at vessel disjoints and overlaps by localized techniques.

Another advantage of the present invention is that it is compatible with both white blood angiography and black blood angiography.

Another advantage of the present invention is that it provides rapid and accurate vessel boundary estimation using propagation of geometric contours. The propagating can advantageously incorporate the gray scale image information through fuzzy membership classification of image elements in the neighborhood of the contour.

Another advantage of the present invention is that it provides locations of furcation and vessel overlap points globally throughout the angiographic volume. This information can be used by vessel trackers or other vessel segmentation systems to improve accuracy and speed.

Yet another advantage of the present invention is that it improves tracking speed and accuracy by providing a plurality of vessel center points or tags that are representative of the global vascular system.

Still yet another advantage of the present invention is that it advantageously retains the sharp vascular edges and accurate vessel lumen information typically achieved by black blood data acquisition during the vessel segmentation processing.

Numerous additional advantages and benefits of the present invention will become apparent to those of ordinary skill in the art upon reading the following detailed description of the preferred embodiment.

BRIEF DESCRIPTION OF THE DRAWINGS

The invention may take form in various components and arrangements of components, and in various steps and arrangements of steps. The drawings are only for the purpose of illustrating preferred embodiments and are not to be construed as limiting the invention.

FIG. 1 shows a schematic drawing of a pair of intertwined vascular structures that have several bifurcation points;

FIG. 2 shows a schematic drawing of a vessel crossing with typical angiographic slice images superimposed;

FIG. 3A shows a typical angiographic slice in the overlap region of FIG. 2 with the vessels artificially differentiated;

FIG. 3B shows a typical angiographic slice in the overlap region of FIG. 2 without the artificial differentiation;

FIG. 4 shows an exemplary magnetic resonance angiography (MRA) system formed in accordance with an embodiment of the invention;

FIGS. 15 and 16 show an exemplary embodiment of the vessel centers processor of FIG. 5;

FIG. 22A shows a synthetic structure consisting of two isolated circular flood-filled regions;

FIG. 22B shows the results of the recursive erosion method of FIGS. 20 and 21 as applied to the synthetic structure of FIG. 22A;

FIG. 22C shows a synthetic structure consisting of two overlapping circular flood-filled regions;

FIG. 22D shows the results of the recursive erosion method of FIGS. 20 and 21 as applied to the overlapping synthetic structure of FIG. 22C;

DETAILED DESCRIPTION OF THE PREFERRED EMBODIMENTS

Figure 5:
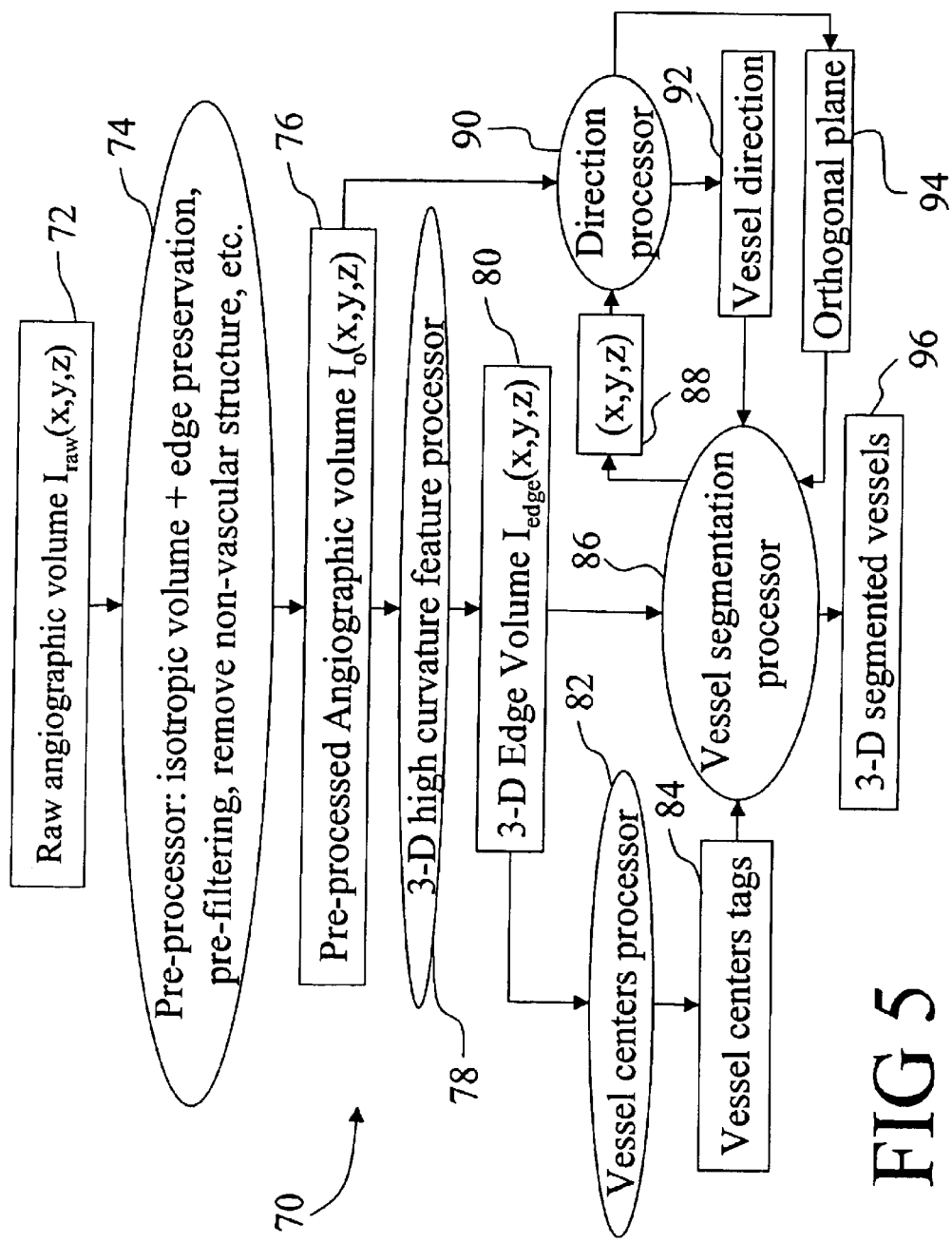
FIG. 5 shows an overview of an exemplary angiographic segmentation method formed in accordance with an embodiment of the invention.

With reference to FIG. 4, a magnetic resonance imaging system that suitably practices angiographic imaging in accordance with an embodiment of the invention is described. Although the invention is described herein with respect to a magnetic resonance imaging embodiment, those skilled in the art will appreciate that the invention is applicable to a broad range of angiographic modalities and techniques, including but not limited to contrast-enhanced magnetic resonance angiography, non-contrast enhanced magnetic resonance angiography, computed tomographic angiography, and fused magnetic resonance/computed tomography angiographic techniques. The invention is also suitably practiced in conjunction with either white blood angiography (WBA) or black blood angiography (BBA).

With reference to FIG. 4, a magnetic resonance imaging (MRI) scanner 10 typically includes superconducting or resistive magnets 12 that create a substantially uniform, temporally constant main magnetic field $B_0$ along a z-axis through an examination region 14. Although a bore-type magnet is illustrated in FIG. 4, the present invention is equally applicable to open magnet systems and other known types of MRI scanners. The magnets 12 are operated by a main magnetic field control 16. Imaging is conducted by executing a magnetic resonance (MR) sequence with the subject being imaged, e.g. a patient 42 in a magnetic resonance angiography (MRA) session, placed at least partially within the examination region 14, typically with the region of interest at the isocenter.

The magnetic resonance sequence entails a series of RF and magnetic field gradient pulses that are applied to the subject to invert or excite magnetic spins, induce magnetic resonance, refocus magnetic resonance, manipulate magnetic resonance, spatially and otherwise encode the magnetic resonance, to saturate spins, and the like. More specifically, gradient pulse amplifiers 20 apply current pulses to a whole body gradient coil assembly 22 to create magnetic field gradients along x-, y-, and z-axes of the examination region 14.

An RF transmitter 24, preferably digital, applies RF pulses or pulse packets to a whole-body RF coil 26 to transmit RF pulses into the examination region. A typical RF pulse is composed of a packet of immediately contiguous pulse segments of short duration which taken together with each other and any applied gradients achieve a selected magnetic resonance manipulation. The RF pulses are used to saturate, excite resonance, invert magnetization, refocus resonance, or manipulate resonance in selected portions of the examination region.

For whole-body applications, the resulting resonance signals, generated as a result of a selected manipulation, are also picked up by the whole-body RF coil 26. Alternately, for generating RF pulses in limited regions of the subject, local RF coils are placed contiguous to the selected region. For example, as is known in the art, an insertable head coil 28 is inserted surrounding a selected brain region at the isocenter of the bore. Other surface coils or other such specialized RF coils may also be employed. For example, the RF system optionally includes a phased array receive coil (not shown) which enables partial parallel imaging (PPI) techniques known to the art. In one suitable embodiment, the whole-body RF coil 26 induces resonance and the local RF coil or coil array receives magnetic resonance signals emanating from the selected region. In other embodiments, the local RF coil both excites and receives the resulting magnetic resonance signals.

Regardless of the RF coil configuration and the application thereof, the resultant RF magnetic resonance signals that are picked up by one or another of the RF coils is received and demodulated by an RF receiver 32. A sequence control processor 34 controls the gradient pulse amplifiers 20, the RF transmitter 24, and the RF receiver 32 to produce integrated MRI pulse sequence and readout waveforms that generate the magnetic resonance (MR) signals and optional echoes, provide appropriate encoding gradients to spatially encode the resultant MR response, and coordinate MR pickup and receive operations.

The MRI sequence typically includes a complex series of magnetic field gradient pulses and/or sweeps generated by the gradient amplifiers 20 which along with selected RF pulses generated by RF coils 26, 28 result in magnetic resonance echoes that map into k-space. The resultant magnetic resonance data is stored in a k-space memory 36. The k-space data is processed by a reconstruction processor 38, which is typically an inverse Fourier transform processor or other reconstruction processor known to the art, to produce a reconstructed image representation that is stored in an image memory 40.

In magnetic resonance angiography (MRA), a patient 42 is imaged by the MRI system 10 using imaging conditions that provide either an enhanced high intensity signal from the vascular regions (white blood angiography) or a suppressed low intensity signal from the vascular regions (black blood angiography) for the vascular regions. The enhanced or suppressed vascular signal provides contrast for the vascular system in the resultant image. In the exemplary embodiment of FIG. 4, the carotid area of the patient 42 is imaged. Optionally, the patient receives a magnetic resonance contrast agent 44 to improve the vascular contrast, i.e. contrast-enhanced MRA is performed. An angiographic sequence such as a time of flight (TOF) white blood sequence, a gradient recalled black blood sequence which can be used in combination with large bipolar gradients or pre-saturation RF pulses, a spin-echo (SE) type black blood sequence which utilizes wash-out effects and which does not require large bi-polar gradients or pre-saturation RF pulses, or other appropriate angiographic sequence is employed. The selected angiographic sequence is applied by the sequence control processor 34 and effectuates acquisition of the MRA data.

Regardless of the choice of MRA imaging modality, the k-space data is collected in the k-space memory 36 and reconstructed by the reconstruction processor 38 to generate the MRA volume image data 40. The MRA volume image data is in the form of a three-dimensional gray scale image representation of the examined area of the patient, which has good contrast for the vascular system relative to other body tissues of the patient 42. Typically a three dimensional image data comprising multiple slices is acquired to provide volume imaging of the patient 42. However, it is also contemplated that only a single image slice is acquired in a patient imaging session.

A pre-processor 46 conforms the angiographic data to a standardized format preparatory to further processing. For example, the pre-processor 46 optionally smooths the data, converts the data into an isotropic format, re-sizes the image, performs pre-filtering to remove noise or extraneous features such as non-vascular contrast that interferes with the vascular image, and the like. For BBA, the pre-processor preferably intensity-inverts the image so that the vascular areas are represented by high intensities.

An edge volume processor 48 receives the output of the pre-processor 46, and applies a mathematical transformation such as second order spatial differentiation to obtain an edge-enhanced volume that particularly emphasizes the edges of the vasculature.

A vessels center tagger 50 receives the output of the edge volume processor 48 and searches the edge volume for vessel centers, e.g. on a slice-by-slice basis. The located vessel center points in each plane are tagged. Vessel centers corresponding to overlapping vessel images are advantageously identified and particularly noted. The vessel centers along with the overlap tags are supplied along with the edge volume image and the pre-processed volume image to a vessel segmentation engine 52.

The segmentation processor 52 processes the angiographic data to segment the vascular structure. The segmenting can be performed in several ways, including: identifying the vasculature as a set of voxels corresponding to the imaged vascular structures; separating of the vascular regions of the image from the non-vascular regions of the image; assigning a first value to voxels corresponding to imaged vascular structures, and a second value to voxels corresponding to imaged non-vascular structures; and removing contrast corresponding to non-vascular structures from the image.

The segmented vascular information is preferably graphically displayed on an appropriate user interface 54, typically as a two-dimensional or three-dimensional graphical image representation. The vascular information can of course also be stored electronically or on a magnetic storage medium, printed on paper, and et cetera (not shown).

With reference to FIG. 5, a method 70 for post-acquisition processing of acquired raw angiographic volume image data $I_{raw}(x,y,z)$ 72 is described in overview. The raw data $I_{raw}(x,y,z)$ 72 is pre-processed 74 to produce a pre-processed angiographic volume $I_o(x,y,z)$ 76 which conforms to a pre-selected data format and which has non-vascular contrast substantially removed therefrom. For example, the pre-processor 74 can convert the image format to one formed of isotropic voxels, pre-filter the data to remove noise, re-size the data, remove extraneous non-vascular contrast, and so forth. In the case of black blood angiographic (BBA) data, the pre-processor 74 preferably removes non-vascular "black" contrast such as bone linings, air pockets, and muscle tissues that typically are imaged with low intensities similar to the black blood. The pre-processor 74 preferably also intensity-inverts BBA data so that the vascular regions correspond to high intensity areas of the pre-processed image $I_o(x,y,z)$ 76.

With continuing reference to FIG. 5, the pre-processed volume $I_o(x,y,z)$ 76 is input to a three-dimensional high curvature feature processor 78 which outputs a three-dimensional edge volume $I_{edge}(x,y,z)$ 80. The edge volume 80 emphasizes the edges of the vascular structures. Processing of angiographic data based on the edge volume 80 is advantageous because it retains the vessel lumen information and will accurately reflect narrowing of the blood vessels due to plaque buildup.

Figure 6C:
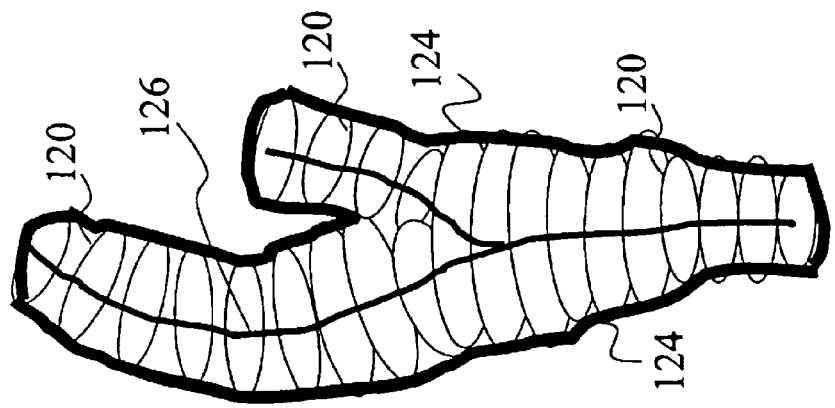
FIG. 6C schematically shows a representation of the bifurcated vascular branch reconstructed using the vessel centers and boundaries of FIGS. 6A and 6B.
Figure 6B:
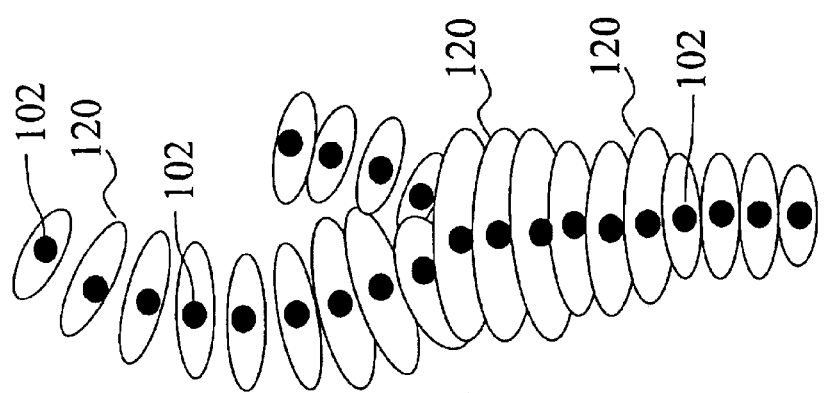
FIG. 6B schematically shows a plurality of estimated vessel boundaries corresponding to the vessel centers of FIG. 6A.
Figure 6A:
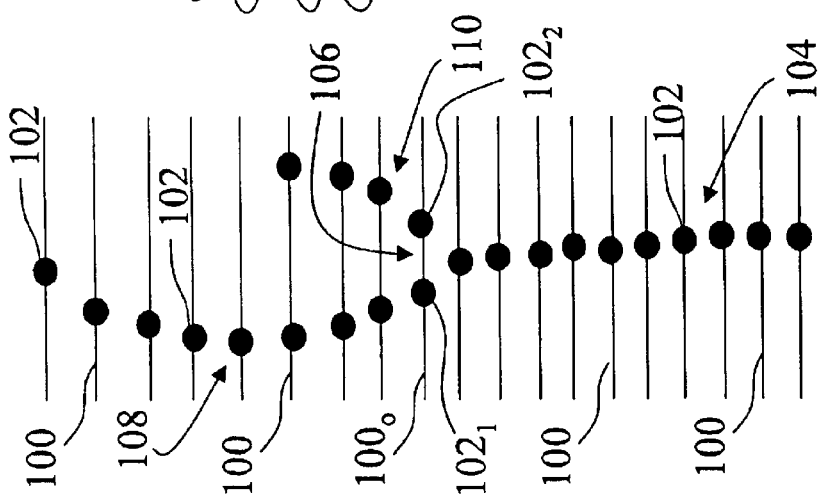
FIG. 6A schematically shows a plurality of vessel centers that are representative of a bifurcated vascular branch.

With continuing reference to FIG. 5 and with further reference to FIG. 6A, a vessel centers processor 82 receives the edge volume $I_{edge}(x,y,z)$ 80 and processes it on a slice-by-slice basis to identify vessel centers 84 substantially throughout the volume of interest which are representative of the imaged vascular system or systems. FIG. 6A shows exemplary parallel slices 100 arranged perpendicular to the paper, with identified vessel centers marked or tagged by filled black circles 102. It will be appreciated that the shown vessel tags 102 are representative of a vessel portion having a lower portion 104, a bifurcation point 106, and two vessel portions 108, 110 extending upward from the bifurcation point 106. Although not immediately apparent from the two-dimensional schematic representation of FIG. 6A, it will be appreciated that each parallel slice 100 extends two-dimensionally into and out of the paper and typically contains vessel centers across the two-dimensional surface, so that the combined slices 100 provide a set of vessel center tags 102 which are representative of the complete three-dimensional vascular system.

With continuing reference to FIGS. 5 and 6A, the vessel center tags 84, 102 preferably include resolved vessel centers of overlapping vascular structures. In the exemplary schematic FIG. 6A, the slice 100$_0$ just above the bifurcation 106 includes two vessel centers 102$_1$, 102$_2$ which are likely to have overlapping vessel boundaries in the angiographic image. The vessel centers processor 82 advantageously recognizes such overlapping conditions.

The vessel center tags 84 form a valuable database of global information about the vascular structures contained in the image. The tags 84 provide a valuable input for many contemplated angiographic post-acquisition processing applications. In one exemplary application (not shown), the centers 84 are plotted to provide a graphical representation of the vascular system. Given a sufficiently high density of vessel centers corresponding to a close spacing of the parallel planes 100, a reasonable representation of the vascular paths is provided thereby. This paths representation does not, however, include the vessel lumen information which is critical for identifying clinically significant plaque buildup and resultant vessel flow constriction which is typically of great interest to medical personnel. Neither does this simple approach provide for artery-vein separation or other sophisticated vascular analyses.

A suitable processing method which incorporates the global vessel center tags 84 to effectuate rapid and accurate vessel segmentation including accurate vessel lumen reconstruction (even in the case of overlapping vessel images) and optional artery-vein separation is described with continuing reference to FIG. 5 and with further reference to FIGS. 6B and 6C. A vessel segmentation processor 86 receives the tags 84. The processor 86 selects a starting location (x,y,z) 88 in the three-dimensional vascular system. The seed 88 can correspond to one of the tags 84. A direction processor 90 receives the location 88 and analyzes the three-dimensional angiographic volume $I_o(x,y,z)$ 76 in the neighborhood of the location 98 to determine the vessel direction 92 and the plane orthogonal to the vessel direction 94 at the location 88. The vessel segmentation processor 86 analyzes the orthogonal plane 94 to determine the vessel boundaries 120 (FIG. 6B) in the plane 94, taking into account tagged vessel overlaps as necessary, and also calculates the next vessel center nearest to the point 88. The segmentation process is repeated until the global set of vessel tags 84 are fully visited. With the vessel boundaries 120 determined, a three dimensional segmented vasculature 96 can be constructed, e.g. by interpolation between the planes 124 and along the vessel centers 126 as shown in FIG. 6C.

By generating and employing the vessel center tags 84, the robustness of the vascular tracking system 70 is greatly improved compared with trackers of the prior art. Prior art tracking systems operate in local space, working from a starting seed and tracking the direction locally. Such systems can fail at bifurcations, vessel gaps, vessel overlaps, and at other localized image structures which cause the vessel direction to become indeterminate. By incorporating the tags 84, a global database of information about the vasculature is included into the tracking. The tags 84 overcome the localized image structures by providing a global representation of the entire vascular system. For example, a vessel gap is identifiable by the existence of additional vessel center tags 84 positioned beyond the gap. Furthermore, the vessel tags identify overlapping vessels so that the tracker can account for the plurality of vessels at a point of overlapping or furcation.

Having provided an overview of the tracking system embodiment 70 formed in accordance with the invention with reference to FIGS. 5 to 6C, the details of the exemplary segmentation system 70 are now described.

Figure 7:
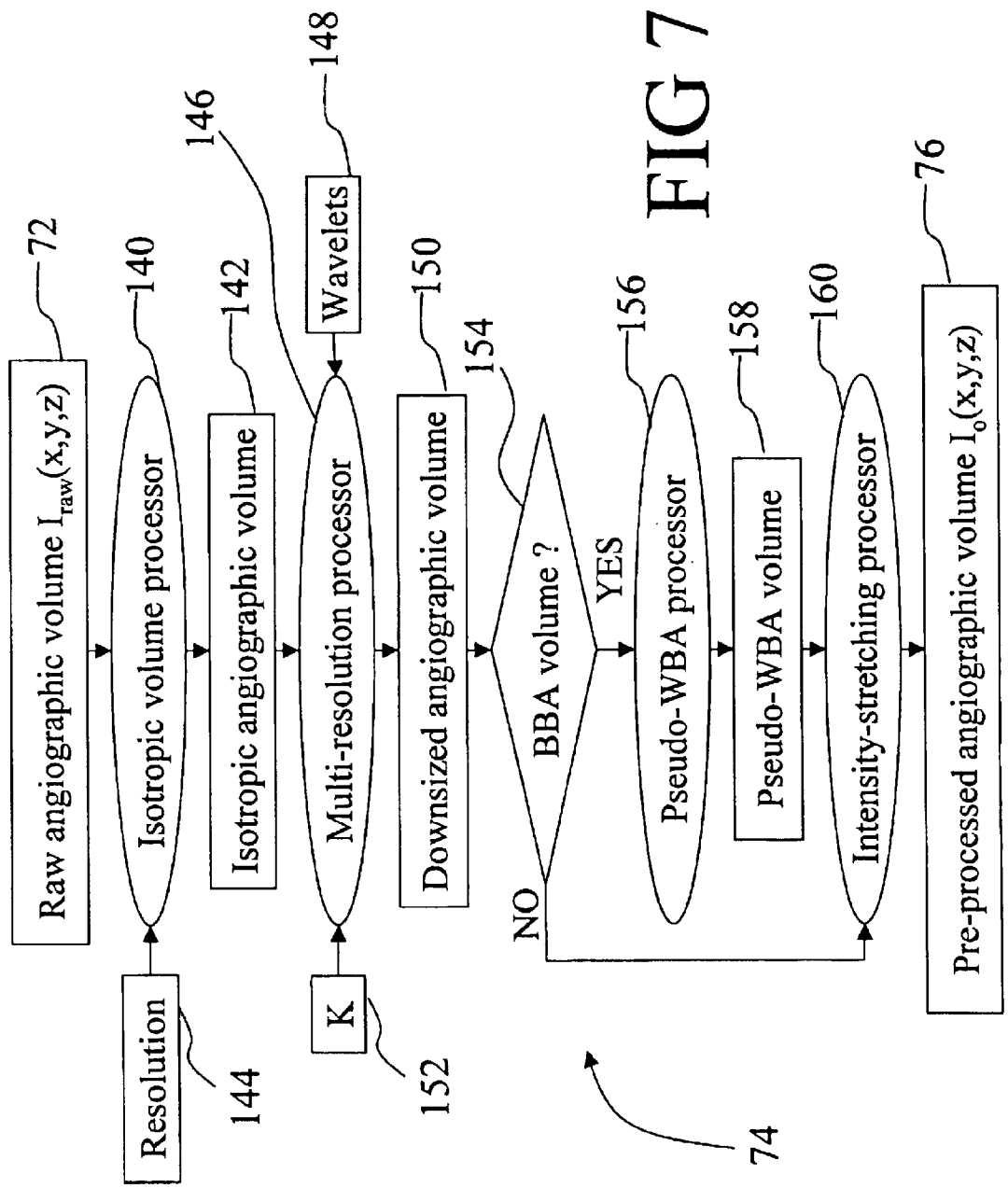
FIG. 7 shows an exemplary embodiment of the pre-processor of the segmenter of FIG. 5.

With reference to FIG. 7, a suitable embodiment of the pre-processor 74 is described. The raw angiographic volume $I_{raw}(x,y,z)$ 72 is input to an isotropic volume processor 140 which converts the gray scale volume image data 72, which may or may not be formed of cubic voxels, into an isotropic gray scale angiographic image volume 142 which is formed of cubic voxels of a selected resolution 144. Of course, if the raw data 72 as-acquired is isotropic, the conversion 140 is not applicable.

With continuing reference to FIG. 7, the isotropic data is optionally down-sized using an edge-preserving processor 146 which in a suitable embodiment employs a shrinking and translating transform such as a discrete wavelet transform (DWT) 148 for edge-preserving re-sizing, to produce a re-sized image 150 which is down-sized by a factor K 152. The DWT advantageously substantially preserves the high frequency edges of the image so that accurate blood vessel lumen information is retained. The wavelet transform is applied according to:

$$\Phi_{(a,b)}(x) = 2^{-\frac{1}{2}} \phi\left(\frac{x-b}{a}\right) \quad (1)$$

where φ is the isotropic image volume 142, a is a scale factor and b is a location/time parameter. The continuous wavelet transform is given by convolution as:

$$\tilde{f}_w(a,b) = \int_{-\infty}^{\infty} f(t) 2^{-\frac{1}{2}} \phi\left(\frac{t-b}{a}\right). \quad (2)$$

The mother function φ (herein the isotropic image volume 142) should satisfy admissibility criterion to ensure that it is a localized zero-mean function. Equation (2) can be discretized by restraining a and b to a lattice of the form $a=2^{-s}$ to get a wavelet basis in which the dilations and translations (scaling and shifting) of the mother function φ is given by:

$$\Phi_{(s,l)}(x) = 2^{-\frac{s}{2}} \Phi(2^{-s}x - l) \quad (3)$$

where s and l are integers that scale and dilate the mother function φ to generate wavelets, such as those of the Daubechies wavelet family. The scale index s indicates the wavelet's width and the location index l gives its position. Those skilled in the art will recognize that by applying equation (3) to the isotropic image volume 142, the image is rescaled or dilated by K 152 which is a power of 2, and translated by an integer. The image is transformed into four down-scaled images, three of which contain horizontal, diagonal, and vertical details, respectively, while the fourth image contains the desired downsized angiographic volume 150.

In the case 154 of a black blood angiographic (BBA) volume, the BBA image is advantageously transformed by a pseudo-white-blood-angiographic (pseudo-WBA) processor 156 which: (i) replaces extraneous black non-vascular contrast with an alternative intensity which does not closely correspond with the black blood intensity; and (2) intensity-inverts the image so that the BBA volume has a "white-blood-type" contrast in which the vascular areas appear at high intensity. The processor 156 produces a pseudo-WBA image volume 158 which has the intensity polarity of WBA and is suitable for further processing in the same manner as a WBA image volume.

With continuing reference to FIG. 7, the image volume 150 (for WBA) or the image volume 158 (for BBA) is input to an intensity-stretching processor 160 which produces the pre-processed angiographic volume $I_o(x,y,z)$ 76. This processor increases the intensity range by increasing the difference between the vessels intensity and the background intensity. In a suitable embodiment, the intensity-stretching processor 160 normalizes the voxel intensities according to:

$$I_{output} = I_{input} \times \frac{2^{N-1}}{I_{max} - I_{min}} \quad (4)$$

where N is the number of bits per voxel, $I_{max}$ is the maximum intensity in a slice and $I_{min}$ is the minimum intensity in a slice. The intensity-stretching processor 160 improves the sensitivity to the vasculature by raising the vessels intensity above the background. It is most effectively used in conjunction with noise-filtering processors which remove isolated, "hanging" noise voxels and otherwise suppress non-vascular intensities.

Figure 8:
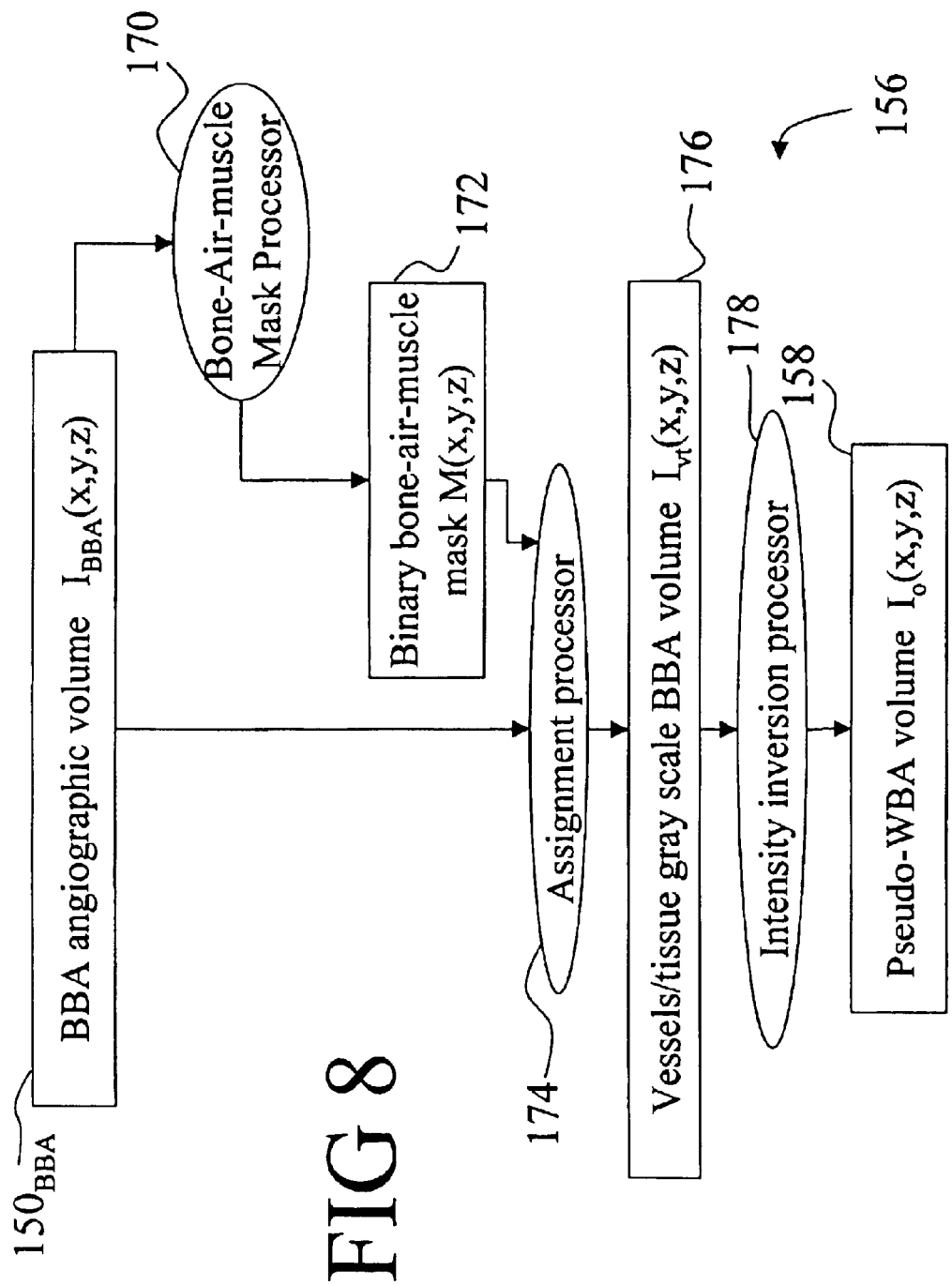
FIG. 8 shows an exemplary embodiment of the pseudo-white blood angiographic (pseudo-WBA) processor of FIG. 7.

With reference to FIG. 8, a suitable embodiment of the pseudo-WBA processor 156 is described. The BBA volume $I_{BBA}(x,y,z)$ 150$_{BBA}$ is processed to remove any non-vascular dark or black regions by constructing 170 a binary bone-air-muscle mask 172 and assigning 174 a gray intensity level to the non-vascular black areas identified by the mask 172. The gray intensity level assigned by the assignment processor 174 advantageously corresponds to the average value of the gray non-vascular areas which are not masked by the mask 172. Thus, the black non-vascular regions are replaced by a uniform average gray intensity.

The output of the assignment processor 174 is a vessels-tissue gray scale BBA volume $I_{vt}(x,y,z)$ 176 which has clearly distinguishable vascular regions of very low intensity, i.e. black blood, on a higher intensity, gray background. The vessels-tissue gray scale BBA volume $I_{vt}(x,y,z)$ 176 advantageously replaces the non-vascular tissues which typically appear black in BBA images by a higher intensity corresponding to the average intensity of the gray areas of the BBA image. Those skilled in the art will recognize that the volume $I_{vt}(x,y,z)$ 176 overcomes the well-known difficulty in BBA image interpretation that certain non-vascular tissues, particularly air pockets, bone linings, and muscle tissues, appear black in BBA images and can interfere with, obscure, and confuse interpretation of the vascular information contained within the BBA image 150$_{BBA}$.

With continuing reference to FIG. 8, the vessels-tissue gray scale BBA volume $I_{vt}(x,y,z)$ 176 is intensity-inverted 178 to produce the pseudo-WBA image volume 158 in which blood vessels are represented by high intensity, i.e. appear white. With the intensity of a voxel of the gray scale BBA volume $I_{vt}(x,y,z)$ 176 designated $x_{vt}$ and the corresponding voxel of the pseudo-WBA image volume 158 designated $x_{WBA}$, the intensity inversion is according to:

$$x_{WBA} = (2^n - 1) - x_{vt} \quad (5)$$

where n is the number of bits per voxel. For example, if n=8 then $x_{WBA} = 255 - x_{vt}$, and so a low intensity black pixel having $x_{vt} = 0$ converts to a high intensity $x_{WBA} = 255$. Although a linear voxel intensity inversion transformation has been described with reference to equation (5), other intensity inversion transformations are also contemplated, such as non-linear transformations which advantageously account for non-linearities in the intensity data.

Figure 9:
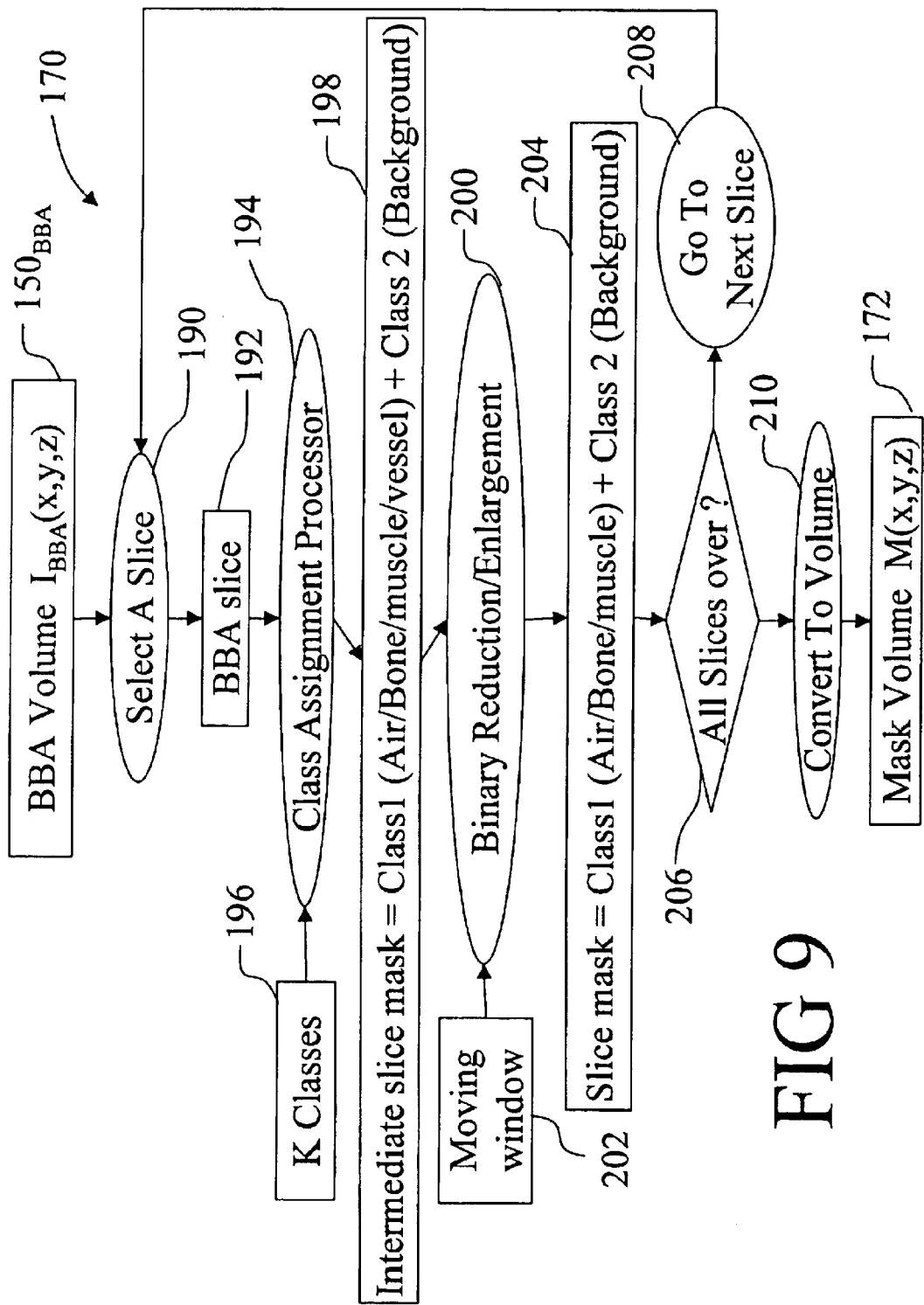
FIG. 9 shows an exemplary embodiment of the bone-air-muscle mask processor of FIG. 8.

With reference to FIG. 9, a suitable embodiment of the bone-air-muscle mask processor 170 is described. A slice selector 190 selects a slice 192 from the BBA volume 150$_{BBA}$. Each pixel in the slice 192 is classified 194. The number of classes 196, designated herein as K, corresponds to the number of distinct types of pixels in the slice 192. As mentioned previously, typical BBA images contain two types of pixels: (1) black pixels that correspond to vascular structures or to certain non-vascular structures such as air pockets, bone linings, and muscle tissues; and (2) gray pixels that correspond to most organs and other tissue types and form much of the image background. Thus, the number of classes 196 is selected as K=2.

With continuing reference to FIG. 9, the class assignment processor 194, a suitable embodiment of which will be described later, assigns each pixel of the slice 192 as either a black pixel or a gray pixel, corresponding to bone/air/vascular structures and tissue background respectively. The classification results are suitably expressed as an intermediate binary slice mask 198. The mask 198 is intermediate because it does not differentiate between vascular and non-vascular black pixels, whereas the desired mask should identify only the non-vascular black regions.

It will be appreciated that the vascular regions are tubular in structure, whereas non-vascular regions are typically large annular structures corresponding to bone linings or large irregular structures corresponding to air pockets. Thus, the mask processor 170 removes the vascular regions from the intermediate mask 198 using a mathematical reduction/enlargement sequence 200. In a suitable embodiment, an erosion process applies a moving window 202 to erode the edges of the black regions of the mask by a pre-selected amount. The narrow tubular vascular structures are thus completely removed whereas the non-vascular structures, which are typically larger, have only the edges reduced. A subsequent dilation process enlarges the non-vascular areas back to their original uneroded size. The resulting slice mask 204 contains only the non-vascular structures with the blood vessels removed, and is suitable for use in identifying the non-vascular black regions of the image.

With continuing reference to FIG. 9, the slice mask generation process is repeated on a slice-by-slice basis 206, 208 to produce a mask slice 204 corresponding to each slice of the BBA volume 150$_{BBA}$. The mask slices 204 are combined 210 to generate a mask volume 172.

Figure 10:
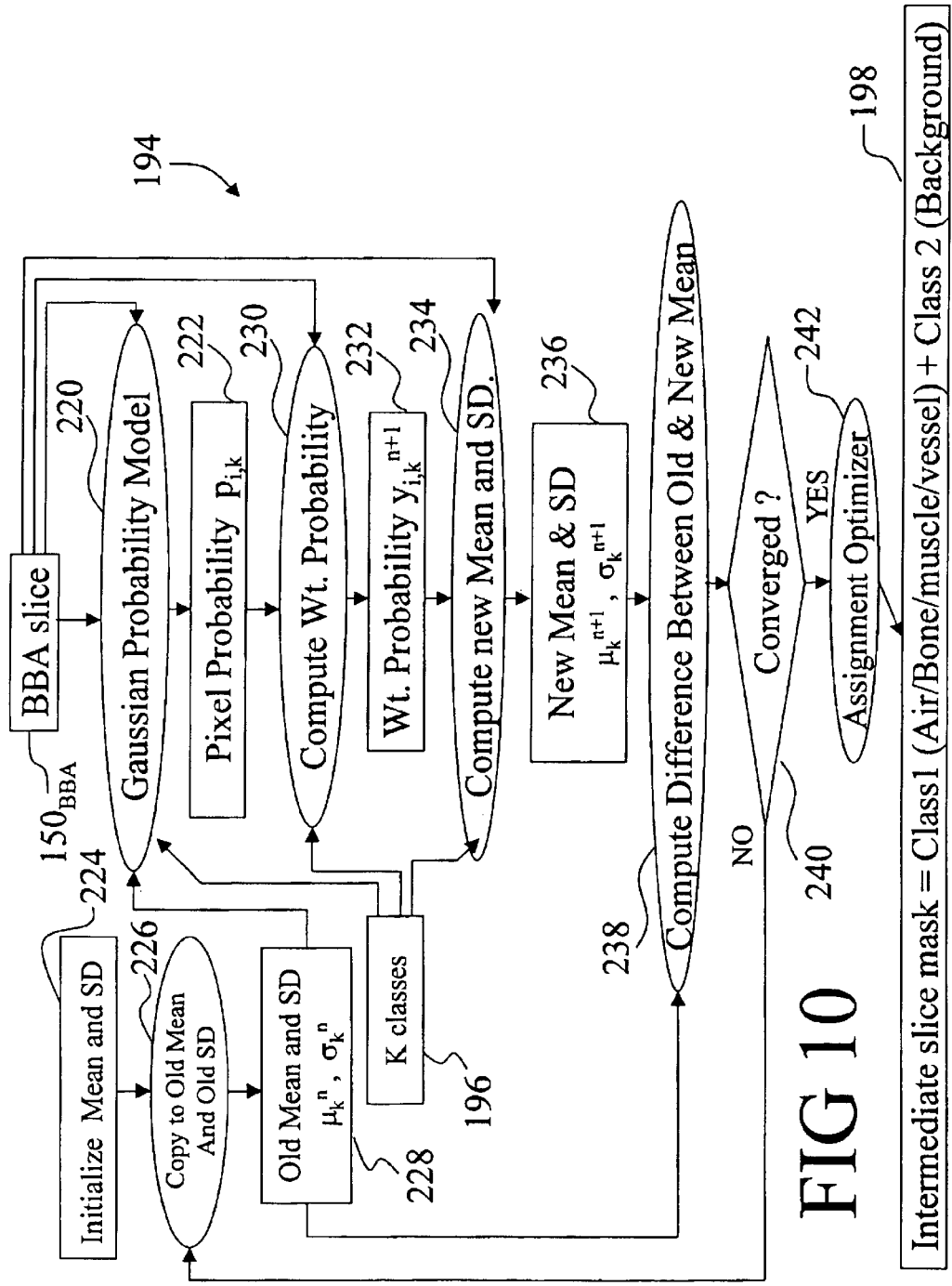
FIG. 10 shows an exemplary embodiment of the class assignment processor of FIG. 9.

With reference to FIG. 10, a suitable embodiment of the class assignment processor 194 is described. The described processor 194 embodiment is based on constructing a parameterized statistical model including a Gaussian distribution. The mean and standard deviation of the Gaussian distribution are the optimized parameters. The class assignment processor 194 is described with reference to N pixels in the image slice 192, and with respect to the K classes 196.

Although K=2 for typical two-class BBA data, inclusion of additional classes is also contemplated for specific imaging situations, and so the class assignment processor 194 is described for an arbitrary number of classes K 196. The pixels are designated herein by i where $1 \leq i \leq N$, and the classes are designated by k where $1 \leq k \leq K$. The pixel intensities are expressed herein as $x_i$. The pixel classifications are expressed as $y_{i,k}$, which indicates the statistical probability that the pixel i is a member of the class k. A Gaussian probability model 220 is used to calculate unweighted pixel probabilities 222 according to:

$$p_{i,k} = p(x_i | y_{i,k}, \Phi) = \frac{1}{\sqrt{(2\pi)^D \sigma_k^2}} e^{\frac{-(x_i - \mu_k)^2}{2\sigma_k^2}} \quad (6)$$

where: $p_{i,k} = p(x_i | y_i, \Phi)$ is the unweighted Bayesian probability that a pixel of intensity $x_i$ is in the class k; $\mu_k$ and $\sigma_k$ are the mean and standard deviation of the Gaussian probability distribution model; $\Phi$ are the model parameters, e.g. $\Phi = \{\mu_k, \sigma_k\}$; and D is a dimensional parameter, here D=1.

With continuing reference to FIG. 10, the described embodiment of the class assignment processor 194 optimizes the classification probabilities by maximizing the a posteriori probability by iteratively optimizing the Gaussian model parameters $\Phi = \{\mu_k, \sigma_k\}$ and a weighting $w_k$. The pixel classification values $y_{i,k}$ and the distribution parameters $\Phi = \{\mu_k, \sigma_k\}$ are assigned initial values 224, and an initial probability weighting $w_k$ is computed. Suitable initial values are given by:

$$w_k^o = \frac{1}{k}\xi \quad \mu_k^o = \frac{(k+1)2^N}{k} \quad \sigma_k^o = \sqrt{\frac{N}{2} \times \frac{N}{2}} = \frac{N}{2} \quad (7)$$

where $\xi$ is the covariance and the superscript "o" indicates the zeroth iteration. The initial mean and standard deviation 224 are copied 226 into the past-iteration or old mean and standard deviation memory 228. Using the Gaussian probability model 220, the unweighted pixel probability $p_{i,k}$ 222 is calculated using the old mean and standard deviation 228, and an updating of the weighted classification values $y_{i,k}^{n+1}$ is performed 230 according to:

$$y_{i,k}^{n+1} = \frac{p_{i,k}^n w_k^n}{\sum_k p_{i,k}^n w_k^n}, \quad (8)$$

where the superscript n indicates the current iteration, the superscript n+1 indicates the next iteration, and $w_k^n$ is a weighting given by:

$$w_k^n = \frac{\sum_i y_{i,k}^{n+1}}{\sum_k y_{i,k}^{n+1}}. \quad (9)$$

The updated classification probabilities $y_{i,k}^{n+1}$ 232, which are weighted probabilities, are thus obtained. An iterative updating of the statistical model parameters is also performed 234 according to:

$$\mu_k^{n+1} = \frac{\sum_i y_{i,k}^n x_i}{\sum_k y_{i,k}^n}, \quad \sigma_k^{n+1} = \sqrt{\frac{\sum_i y_{i,k}^n (x_i - \mu_k^n)^2}{\sum_k y_{i,k}^n}} \quad (10)$$

to generate updated statistical model parameters 236.

With continuing reference to FIG. 10, the iterative process is terminated using a suitable convergence criteria. For example, convergence can be indicated by computing 238 a difference between the old mean $\mu_k^n$ and the new mean $\mu_k^{n+1}$ for each class k and checking 240 for convergence by comparing the differences with pre-set criteria. The iterative process can also optionally be terminated after a pre-set number of iterations.

Once the iterative process is complete, an assignment optimizer 242 assigns the optimized classification to each pixel of the intermediate slice mask 198. For each pixel, the final weighted probabilities $y_{i,k}$ of each class for a pixel are obtained and the class k that has the highest corresponding weighted probability $y_{i,k}$ for that pixel is selected as the classification of that pixel.

A suitable embodiment of an exemplary pre-processor 74 has been described with reference to FIGS. 7–10. The exemplary pre-processor 74 generates an isotropic, edge-preserving, optionally re-sized and intensity-inverted image $I_o(x,y,z)$ 76 which has WBA intensity polarity. Of course, additional or other pre-processing steps are also contemplated, such as additional noise filtering, smoothing, etc.

With reference returning to FIG. 5, the pre-processed angiographic volume $I_o(x,y,z)$ 76 is input to the three-dimensional high curvature feature processor 78 which outputs an edge volume $I_{edge}(x,y,z)$ 80.

Figure 11:
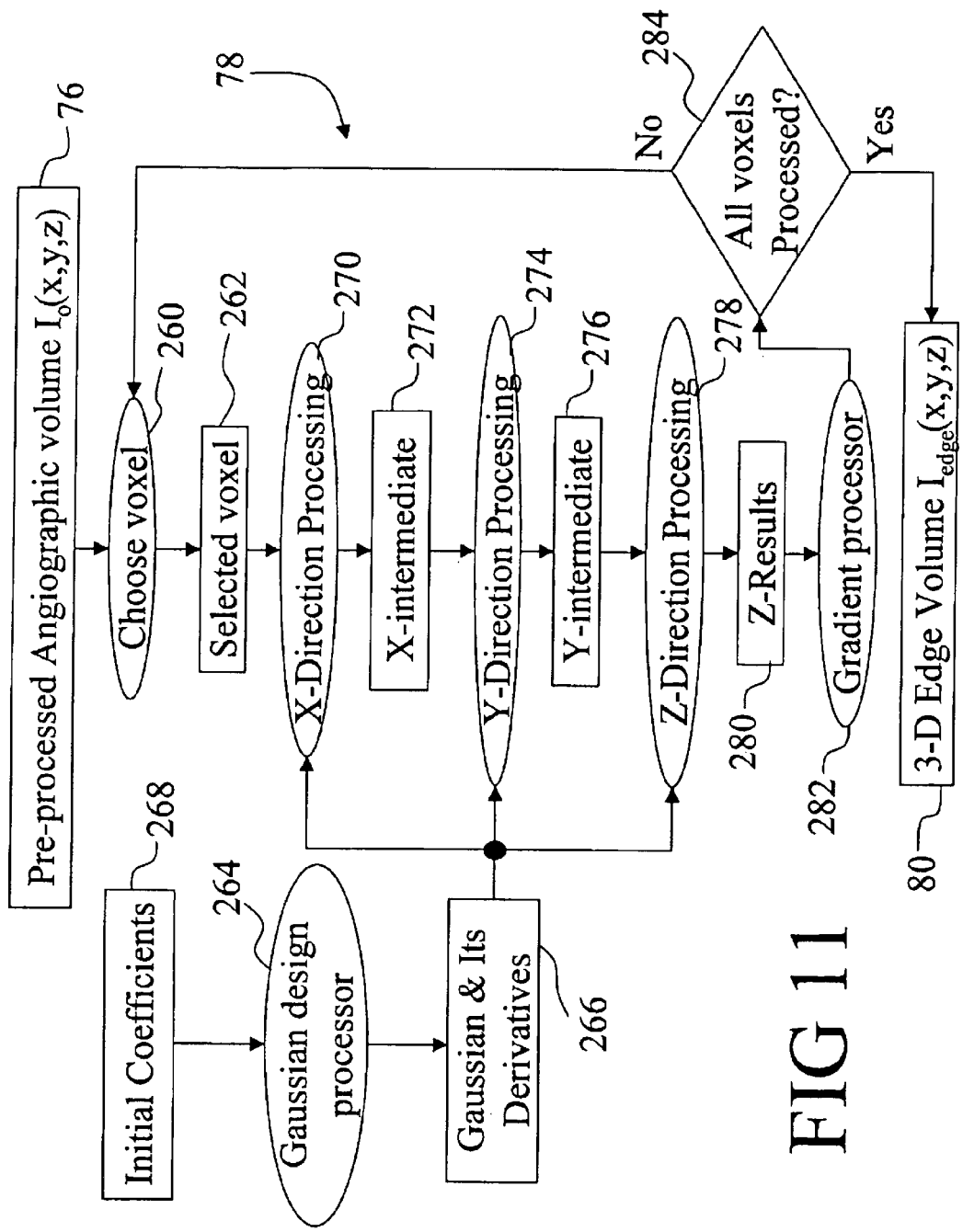
FIG. 11 shows an exemplary embodiment of the three-dimensional high curvature feature processor of FIG. 5.

With reference to FIG. 11, a suitable embodiment of the edge processor 78 is described. The edge processor 78 approximates differentiation of the angiographic volume $I_o(x,y,z)$ 76 by convolving the image 76 with a second order Gaussian derivative. A voxel 262 is chosen 260. A Gaussian design processor 264 calculates a Gaussian and its derivatives 266 based on initial coefficients 268. The calculation of the Gaussian derivatives preferably takes advantage of known closed-form expressions for the Gaussian derivatives. Although the convolving is ordinarily a calculation of order $O(k^3)$ where k is the number of number of voxels forming the Gaussian kernel 266, by convolving in separable mode the calculation is reduced to order $O(3k)$. Thus, the convolving reduces to: a convolution in the x-direction 270 which produces an x-intermediate result 272; a convolution in the y-direction 274 which produces a y-intermediate result 276; and a convolution in the, z-direction 278 which produces the final result 280. The gradient processor 282 combines the one-dimensional derivatives estimated by the convolving to form an edge volume voxel according to:

$$I_{edge}(x, y, z) = \left(\frac{\partial I_o}{\partial x}\right)^2 + \left(\frac{\partial I_o}{\partial y}\right)^2 + \left(\frac{\partial I_o}{\partial z}\right)^2 \quad (11)$$

where I is the pre-processed angiographic volume $I_o(x,y,z)$ 76 and the partial derivatives are evaluated at the location (x,y,z) of the selected voxel 262. After repeating 284 for every voxel, the edge volume $I_{edge}(x,y,z)$ 80 is generated.

It will be appreciated that the Gaussian is a function with a variance $\sigma$. If $\sigma$ is large, the Gaussian convolution can take prohibitively long, especially for higher order derivatives.

For calculation of the edge volume 80, second order derivatives are used. In a preferred embodiment which greatly improves calculation speed, the convolving is performed using a z-transform decomposition of the Gaussian into sinusoidal and cosinusoidal components.

Figure 12:
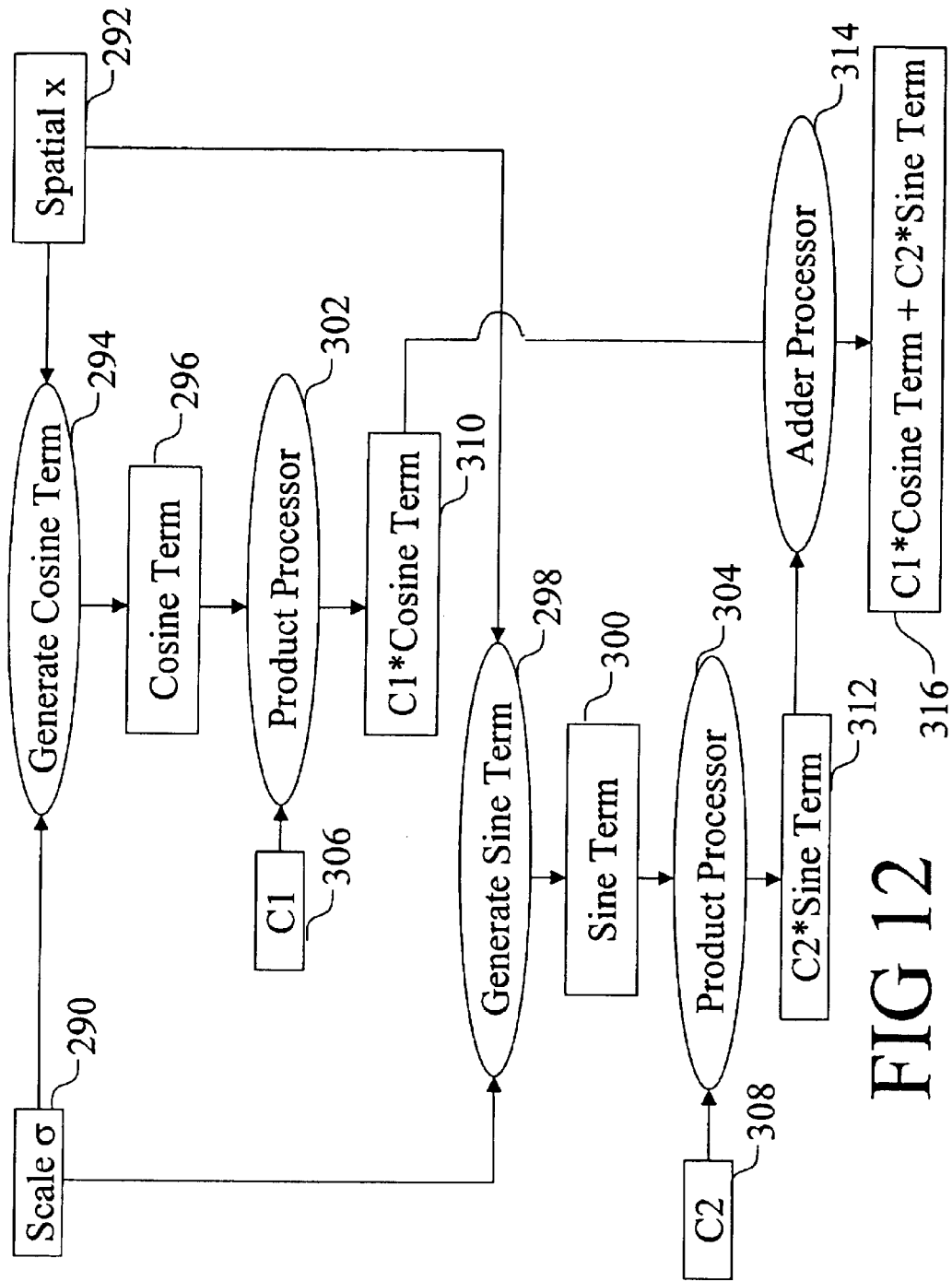
FIG. 12 shows an exemplary embodiment of the decomposition of the Gaussian derivative kernel into cosinusoidal and sinusoidal components.

With reference to FIG. 12, a suitable embodiment for performing the z-transform decomposition is described. For a scale σ 290 and a one-dimensional coordinate x 292, a cosine processor 294 calculates a cosine term 296, and similarly a sine processor 298 calculates a sine term 300. The cosine and sine terms are multiplied 302, 304 by the cosine and sine z-transform coefficients 306, 308, respectively, to produce the cosine and sine z-transform components 310, 312, respectively. These components 310, 312 are additively combined 314 to produce the z-transform 316.

Figure 13:
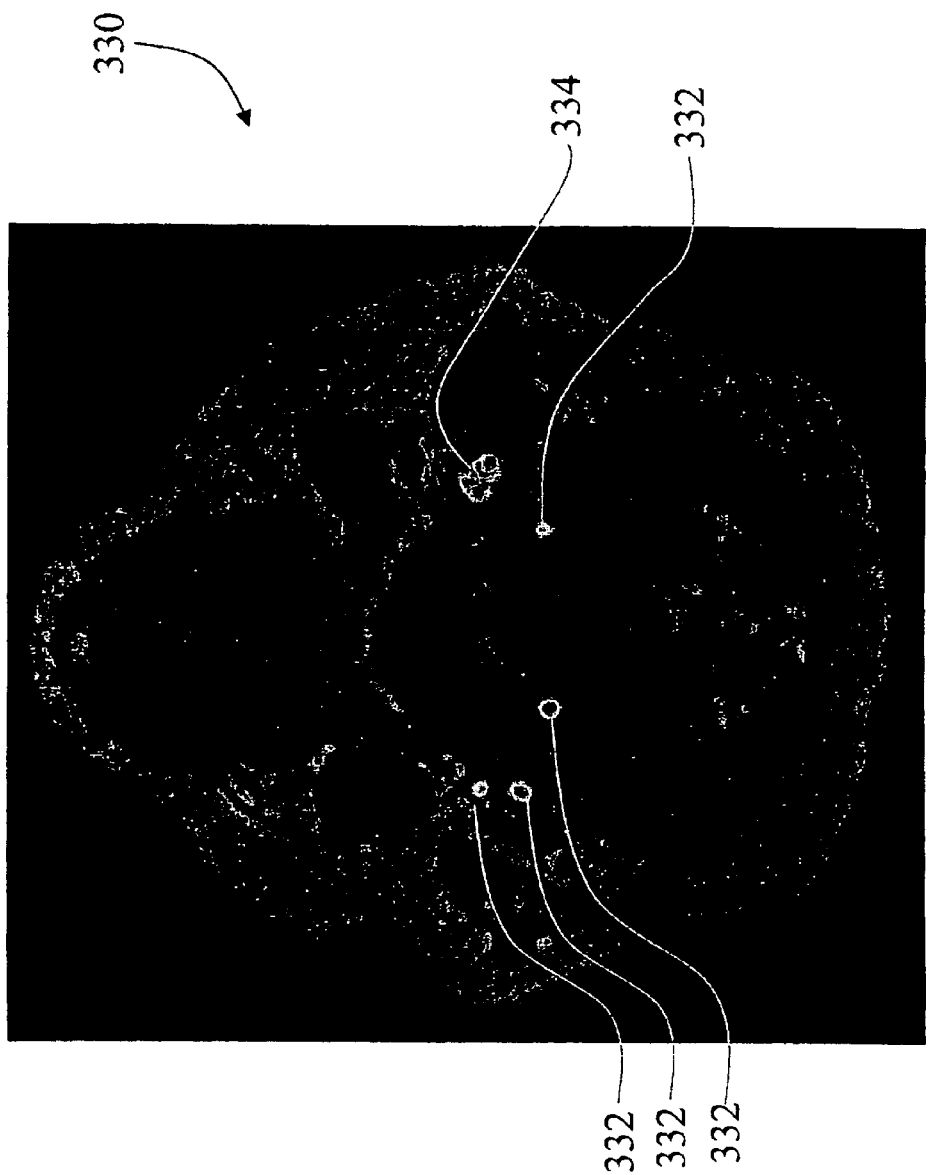
FIG. 13 shows an exemplary time-of-flight white blood angiographic image of the carotid area that includes four isolated vessels as well as one pair of vessels emerging from a bifurcation.

With reference to FIG. 13, an exemplary time-of-flight white blood angiographic image 330 of the carotid area is shown. The image 330 includes four isolated vessels 332 as well as one pair of overlapping vessels 334.

Figure 14:
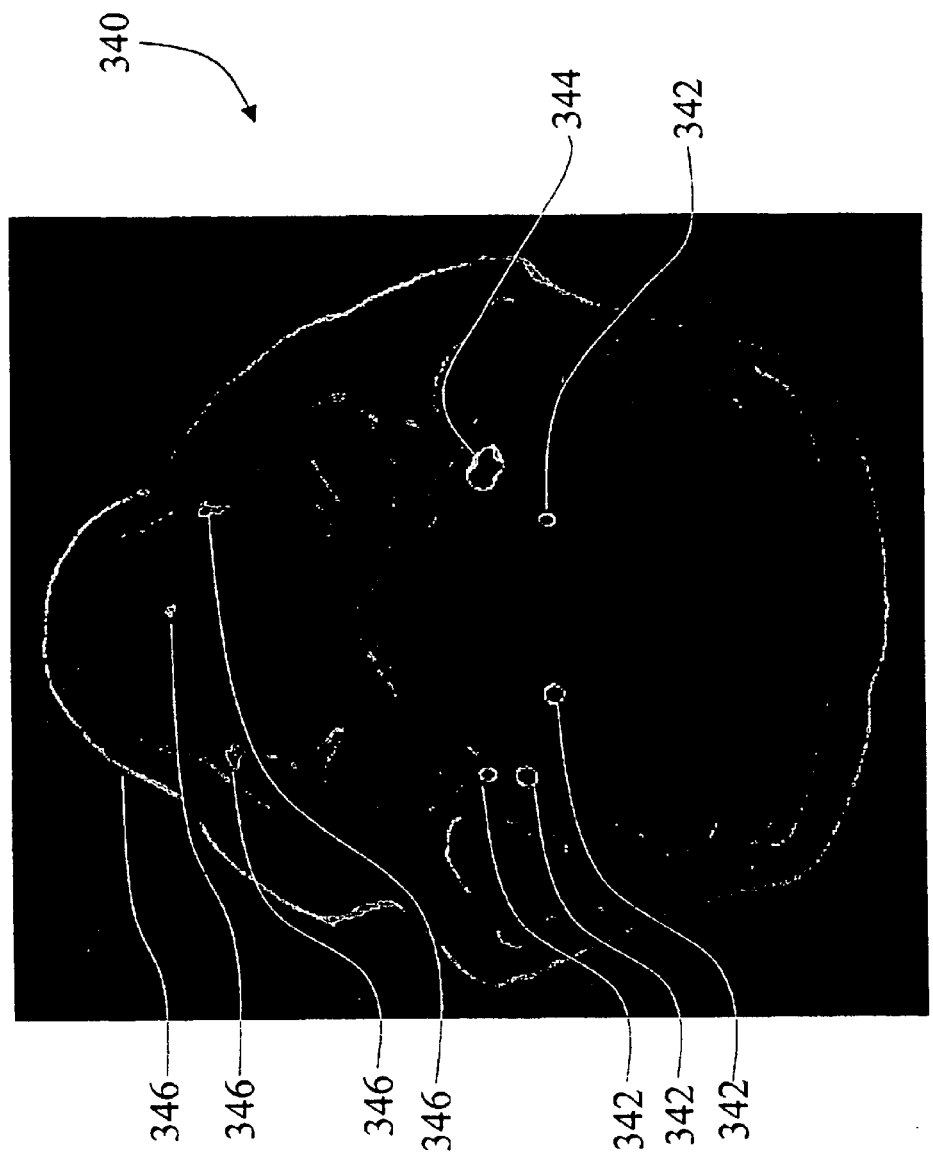
FIG. 14 shows the edge volume corresponding to the image of FIG. 13.

With reference to FIG. 14, the edge volume 340 corresponding to the image 330 is shown. The edge volume is formed according to the method described with reference to FIGS. 11 and 12. Each of the isolated vessels 332 is shown to have a well defined closed contour 342 corresponding thereto. Similarly, the overlapping vessels pair 334 has a corresponding well defined closed contour 344. Besides the contours 342, 344, the remainder of the edge volume 340 is substantially free of features, except for a few low intensity enclosed regions 346 associated with non-vascular features. These non-vascular edges 346 are lower intensity versus the vessel contours 342, 344.

With reference back to FIG. 5, the vessel centers processor 82 receives the edge volume 80 and identifies a plurality of vessel center tags 84 representative of the vascular system. The vessel center tags 84 identify the vessel centers in three-dimensional space, e.g. by coordinates (x,y,z), and also advantageously identify vessel centers corresponding to overlapping vessel images.

Figure 15:
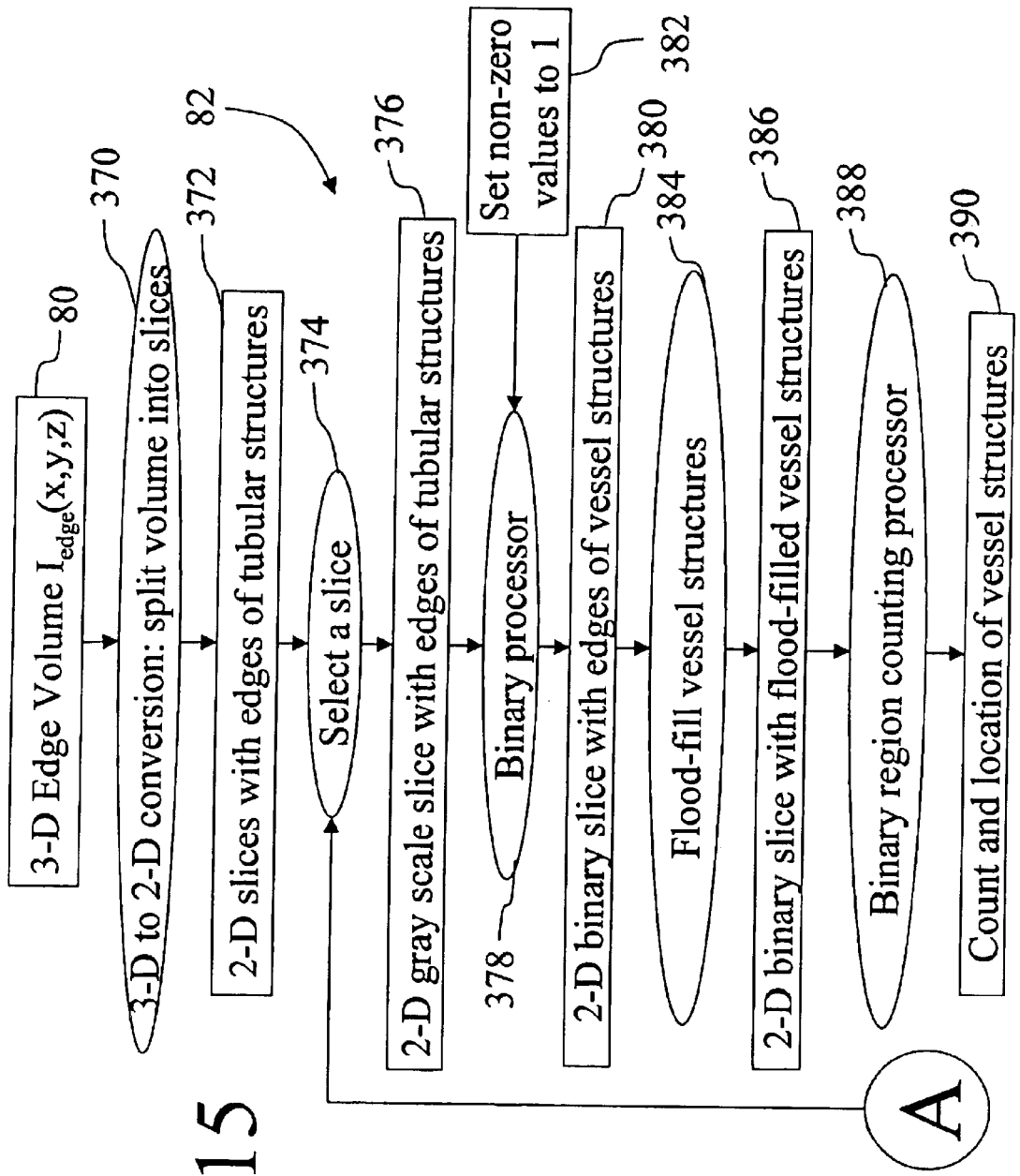

With reference to FIG. 15, a suitable embodiment of the vessel centers processor 82 is described. The approach of this embodiment is to divide 370 the three-dimensional edge volume 80 into two-dimensional edge volume slices 372. Each slice 376 is selected 374 for processing in turn. The edge volume slice 376 is converted 378 into a binary slice 380 by setting the non-zero values to one 382. The binarization 378 can be effectuated, for example, by using a very low thresholding value. As seen in the exemplary edge volume slice 340 of FIG. 14, the edge volume image elements are substantially zero (i.e., black) except at the edge contours 342, 344, and so a low thresholding value will appropriately set the vessel contours 342, 344 to binary one imposed on a binary zero background, thus forming closed binary contour edges of the vessel structures. The vessel structures are flood-filled 384 to form a slice having flood-filled vessel structures 386. There are a number of well-known methods for flood-filling closed contours, and one or more appropriate algorithms are typically available as standard functions in signal processing software development environments. The flood-filled regions are counted 388 to produce a count and location 390 of the vessel structures in the slice 386. In a suitable embodiment, a run length encoder method performs the counting. Run length encoders are well-known algorithms which are commonly employed in JPEG image compression, and functions which implement a run length encoder or a variation thereof are often available in signal processing software toolboxes or libraries.

With continuing reference to FIG. 15 and with further reference to FIG. 16, a vessel centers tagger 400 receives the slice 386 with the flood filled vessel structures and the count and location of the vessel structures 390. For each flood-filled vessel structure of the slice 386, the vessel centers tagger 400 identifies one or more vessel centers 402 corresponding thereto. The vessel centers tagger 400 is suitably embodied by a recursive erosion process to be described later. Advantageously, the vessel centers processor 82 also particularly tags overlapping vessel structures by identifying 404 vessel structures having more than one vessel center 402, since a plurality of vessel centers 402 corresponding to a single vessel structure indicates the singular vessel structure is formed of overlapping vessel images. Appropriate vessel overlap tags 406 are generated by the vessel overlap identifier 404. By cycling 408 through the slices 372 a set of vessel centers and overlap tags 84 is generated that is representative of the imaged vascular system.

Figure 17B:
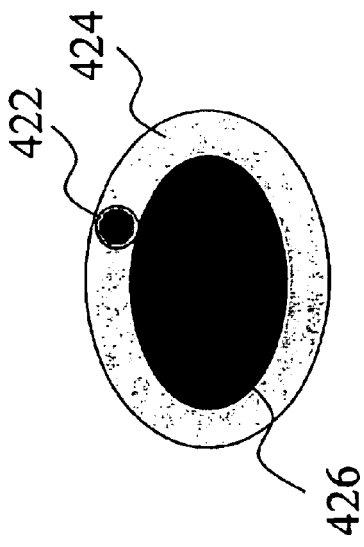
FIGS. 17B, 17C, and 17D schematically show the recursive eroding of the vessel structure of FIG. 17A.
Figure 17D:
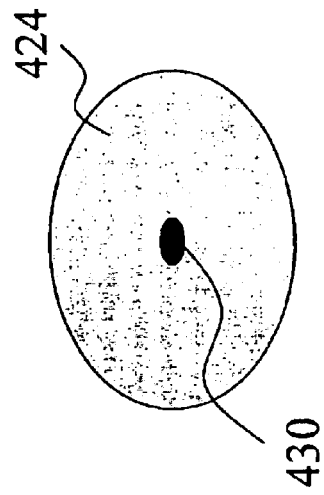
Figure 17A:
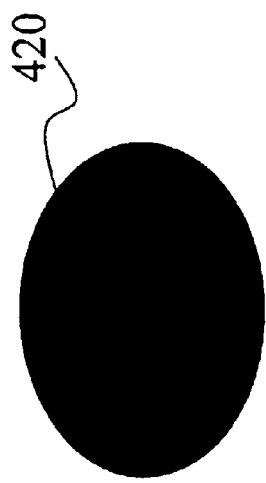
FIG. 17A schematically shows an exemplary vessel structure corresponding to a single vessel center.
Figure 17C:
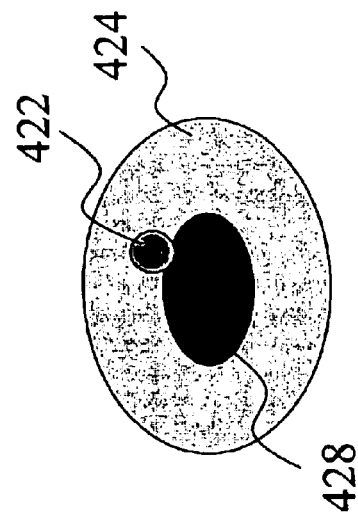

With reference to FIGS. 17A to 17D, a suitable method for implementing the vessel centers tagger 400 is described. A flood filled vessel structure 420 is successively eroded as shown in FIGS. 17B through 17D using a moving window 422. The recursive erosion process iteratively removes outer portions 424 of the vessel structure 420, leaving successively smaller vessel structure portions 426, 428. The final remaining vessel structure portion 430 after the recursive eroding tagged as the vessel center, e.g. its (x,y,z) spatial coordinates are recorded in the table of vessel centers 84. It will be recognized that the flood filled vessel structure 420 of FIG. 17A erodes to a single vessel center 430.

With reference to FIGS. 18A to 18D, the method of FIGS. 17A to 17D is applied to a flood filled vessel structure 440 which images overlapping vessels. During the initial stages of the recursive eroding, the moving window 422 removes outer layers 444 leaving a single reduced vessel structure portion 446. However, as the iterative eroding continues, two distinct vessel structure portions 448, 450 become separately distinguishable. Ultimately, the vessel structure portions 448, 450 erode down to identifiable vessel centers 452, 454. Since the vessel centers 452, 454 correspond to a single flood filled vessel structure 440, the vessel centers processor 82 identifies 404 the flood-filled image 440 formed of overlapping vessel images corresponding to the vessel centers 452, 454.

Figure 19:
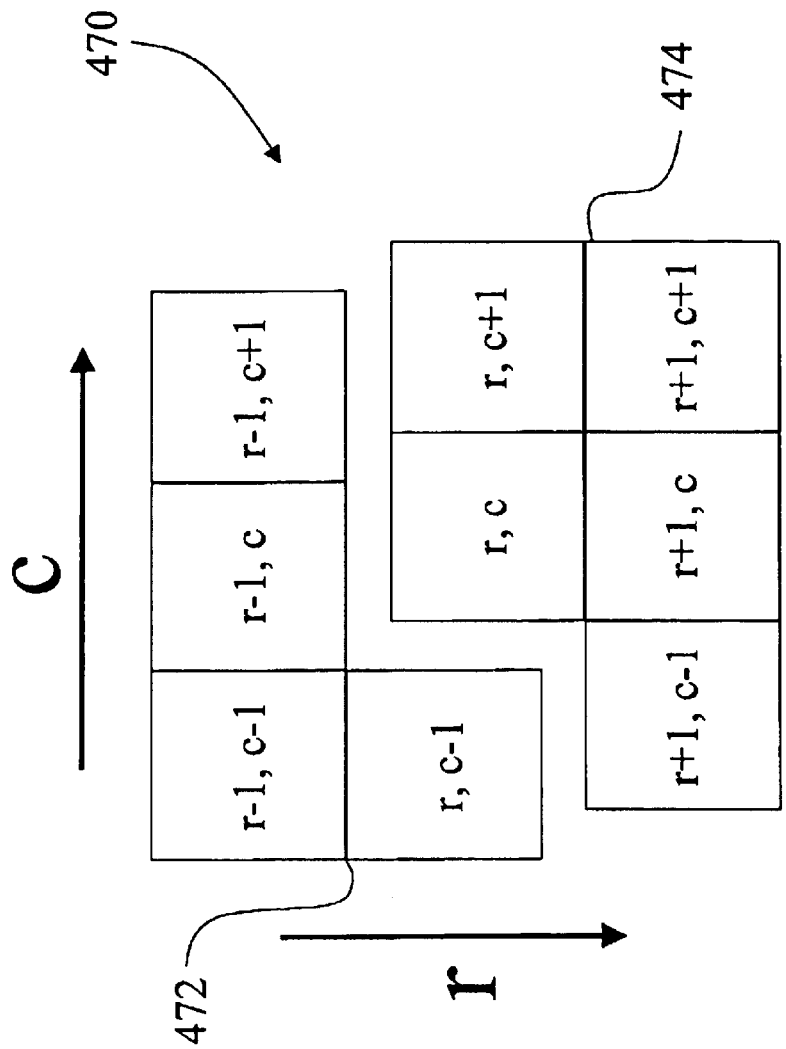
FIG. 19 schematically shows the decomposition of a square moving window for use in recursive erosion into an upper left component and a lower right component.

The moving window 422 shown in exemplary FIGS. 17B, 17C, 18B, and 18C is a filled circular element. With reference to FIG. 19, an exemplary square window 470 is shown which is formed from nine pixel elements arranged about a center (r,c). In order to improve the speed of the recursive erosion, the erosion is advantageously separated into two passes. A first pass runs across the slice from a first corner, e.g. the upper left corner, to a second opposite corner, e.g. the lower right corner, and uses only the upper left portion 472 of the moving window 470. The first pass is followed by a second pass that runs across the slice from the second corner, e.g. the lower right corner, to the first corner, e.g. the upper left corner, and uses only the lower right portion 474 of the moving window 470.

Figure 20:
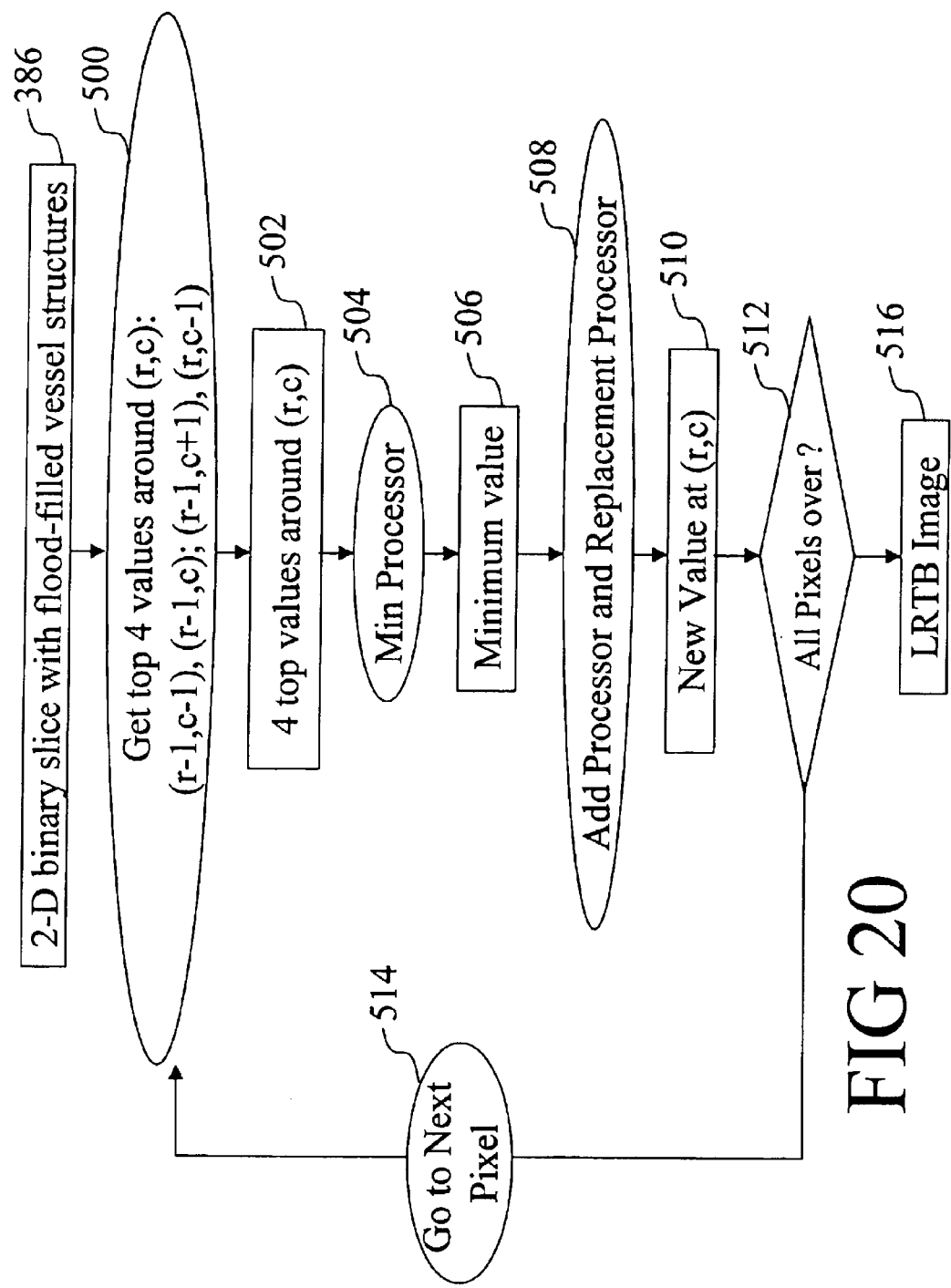
FIG. 20 shows an exemplary method for the first pass of an exemplary two-pass recursive erosion process.

With reference to FIG. 20, the first pass of the decomposed recursive erosion embodiment of the vessel centers tagger 400 is described. For each pixel (r,c) of the slice 386 having flood-filled vessel structures, the top four values A, B, C, D around (r,c) are obtained 500, namely: A=(r−1, c−1); B=(r−1, c); C=(r−1, c+1); and D=(r, c−1). It will be appreciated that these top four values 502 correspond to the upper left portion 472 of the moving window 470 of FIG. 19. A minimum processor 504 selects the minimum value 506 of these four values. And add/replacement processor 508 adds one to the minimum value 506 and replaces the pixel (r,c) with the new value 510. Thus, the transform for the first pass is:

$$(r,c)_{new} = \min\{A,B,C,D\} + 1 \qquad (12)$$

where A, B, C, D are the pixels defined above. The transform of equation (12) is repeated 512, 514 for each pixel to produce an intermediate LRTB image 516.

Figure 21:
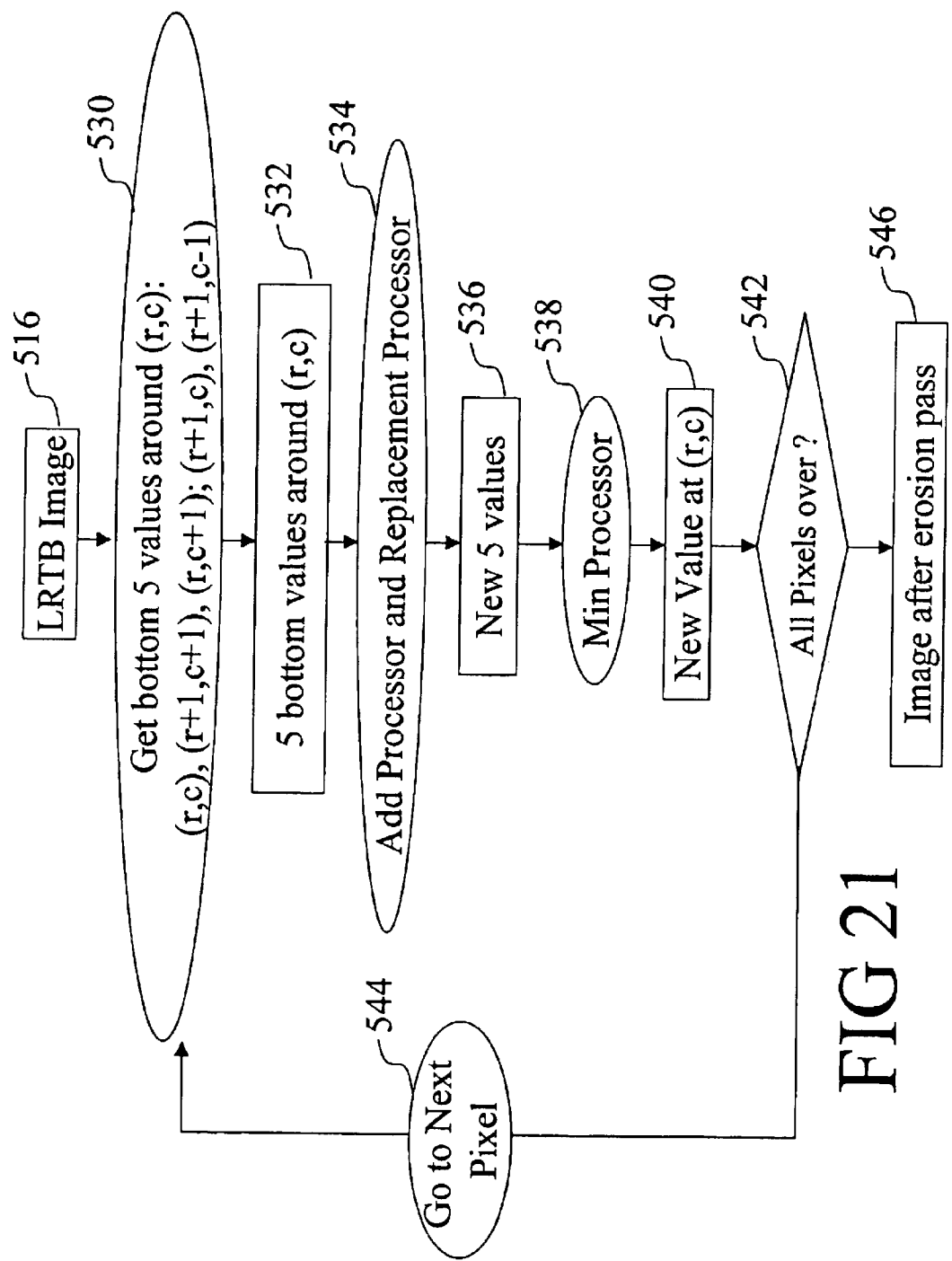
FIG. 21 shows an exemplary method for the second pass of an exemplary two-pass recursive erosion process.

With reference to FIG. 21, the second pass of the decomposed recursive erosion embodiment of the vessel centers tagger 400 is described. For each pixel (r,c) of the intermediate LRTB image 516, the bottom five values around (r,c) are obtained 530, namely: E=(r, c); F=(r+1, c+1); G=(r, c+1); H=(r+1, c); and I=(r+1, c−1). It will be appreciated that these bottom five values 532 correspond to the lower right portion 474 of the moving window 470 of FIG. 19. An add/replacement processor 534 adds one to each of the five values E, F, G, H, I to create five new values 536. A minimum processor 538 selects the minimum value as the new value 540 at the pixel (r,c). Thus, the transform for the second pass is:

$$(r,c)_{new} = \min\{E+1, F+1, G+1, H+1, I+1\} \qquad (13)$$

where E, F, G, H, I are the pixels defined above. The transform of equation (13) is repeated 542, 544 for each pixel to produce the eroded image 546 resulting from an erosion pass. The recursive erosion process of FIGS. 20 and 21 is repeated until the final vessel centers are obtained.

With reference to FIGS. 22A through 22D, exemplary results for recursive erosion according to the process of FIGS. 20 and 21 are presented. In FIG. 21A, a synthetic structure 570 is formed of two fully distinct flood-filled circular contours 572, 574. As shown in FIG. 22B, the recursive erosion process performed according to FIGS. 20 and 21 produces two eroded structures 576, 576 that have clearly defined high-intensity centers corresponding to the centers of the two flood-filled circular contours 572, 574.

With reference to FIGS. 22C through 22D, a synthetic structure 580 is formed of two fully distinct flood-filled circular contours 582, 584. As shown in FIG. 22D, the recursive erosion process performed according to FIGS. 20 and 21 produces two eroded structures 586, 588 that have clearly defined high-intensity centers corresponding to the centers of the two flood-filled circular contours 582, 584. A high intensity connecting line 590 connects the high intensity centers 586, 588 but does not detract from the detectability of the centers 586, 588 because they are positioned at the endpoints of the line 590.

Figure 23:
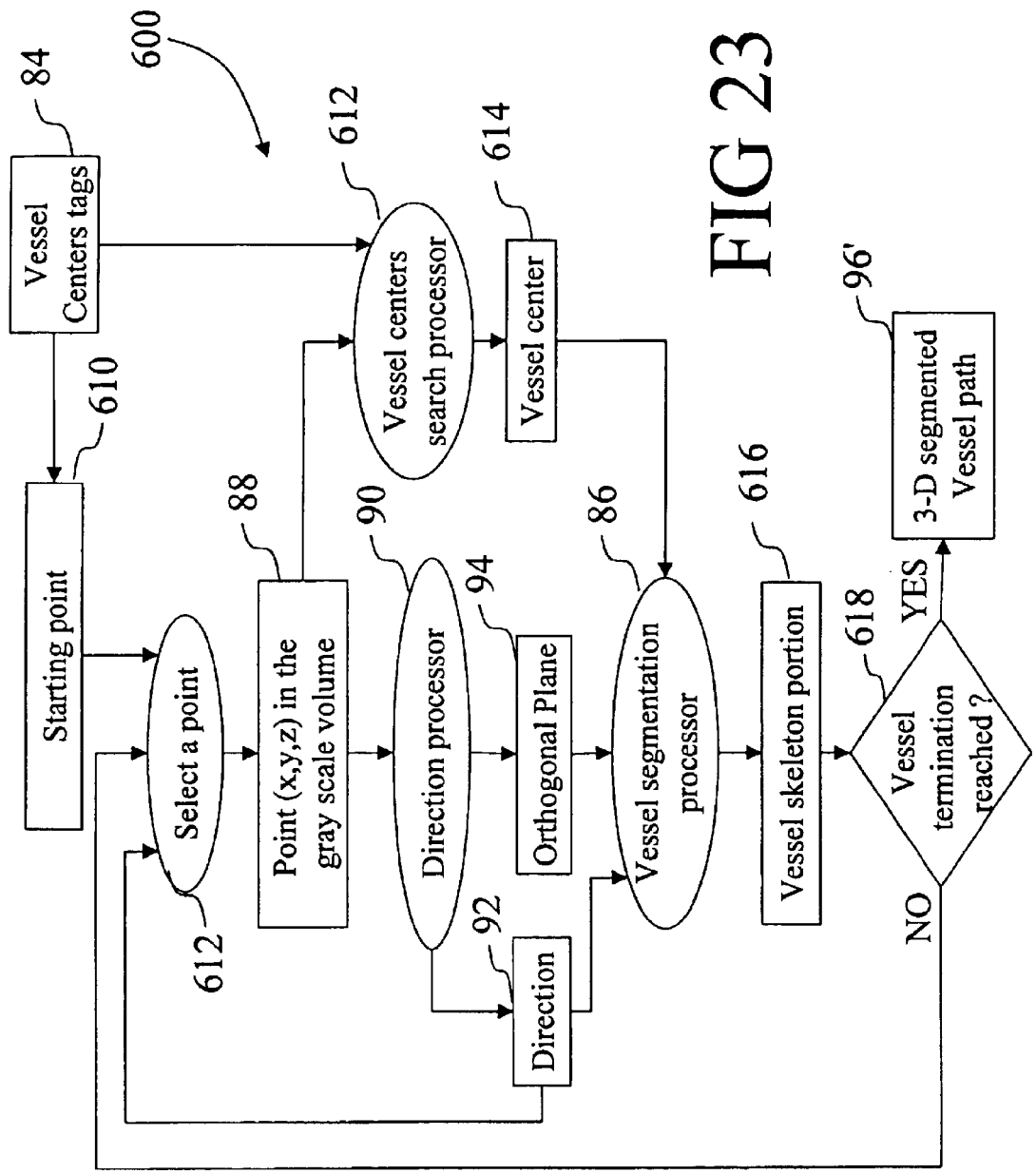
FIG. 23 shows an exemplary path tracking process formed in accordance with an embodiment of the invention that employs a representative set of vessel center tags.

With reference to FIG. 23, the exemplary vessel segmentation processor described in brief overview with reference to FIG. 5 is described in greater detail. The segmentation process of FIG. 23 uses a path tracking process 600. A starting point 610 lying within the vascular system is selected. The starting point is typically a root of the venous or arterial system of interest, and can optionally be selected manually or identified using an automated system, e.g. by selecting the vessel structure having the largest area from the count and location of vessel structures 390 (FIG. 15). The starting point is optionally selected from the table of vessel center tags 84. The tracking point at (x,y,z) 88 is selected 612, initially corresponding to the starting point 610.

Tracking from the point (x,y,z) 88 includes (1) finding the vessel direction; (2) finding the vessel center; (3) finding the extent of the vessel about the vessel center in the plane orthogonal to the vessel direction; (4) locating the next vessel center; and (5) repeating the process. The direction processor 90 finds the vessel direction 92 and the orthogonal plane 94. A vessel centers search processor 612 searches the vessel centers tags 84 to locate the nearest vessel center 614 in space to the point (x,y,z) 88. (Of course, if the point 88 is selected from the vessel centers tags 84, the searching 612 can be omitted). The segmentation processor 86 analyzes the orthogonal plane 94 to determine the extent of the vessel about the vessel center 614. The boundaries of the vessel along with the vessel center 612 form a vessel skeleton portion 616. The process is repeated 618, by selecting 612 a new point 614. The selecting 612 advantageously moves a pre-selected distance along the vessel direction 92, e.g. a distance equivalent to one voxel for the best tracking resolution. Once the vessel termination is reached, a vascular path 96' is obtained.

The tracking system described with reference to FIG. 23 applies to a vascular path 96'. At bifurcation points, the overlap tags 406 (FIG. 16) are advantageously used to identify new starting points 610 at which the path tracking 600 of FIG. 23 is repeated.

Figure 24:
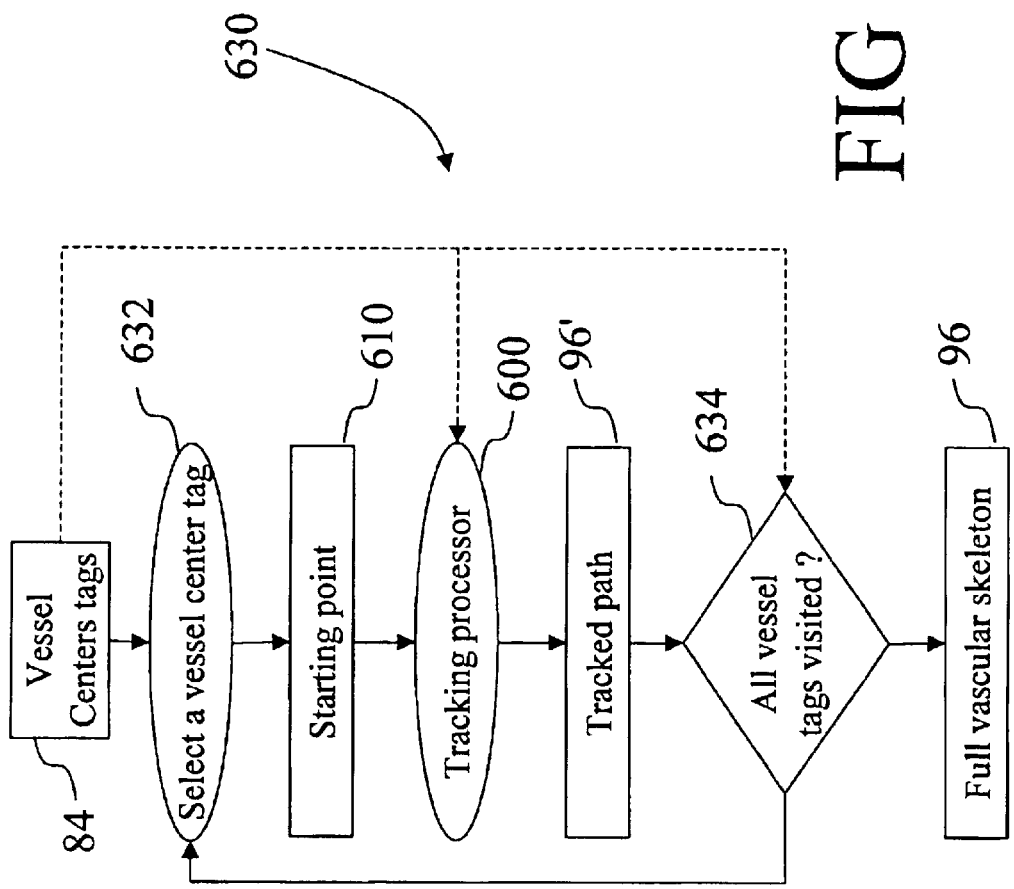
FIG. 24 shows a robust general tracking system formed in accordance with an embodiment of the invention that employs a representative set of vessel center tags to ensure complete tracking of the full vascular skeleton.

With reference to FIG. 24, a robust general tracking system 630 that uses the tags 84 to ensure tracking of all the vascular branches is described. The vessel starting point 610 is selected 632 from the vessel center tags 84. The tracking system 600 of FIG. 23 is applied to generate the tracked path 96' corresponding to the starting point 610. During the tracking 600, each tracked vessel center 614 is marked as visited. After the tracking 610, a check 634 is performed to determine whether all the vessel tags 84 have been marked as visited. If there are unvisited tags, one of the unvisited tags is selected 632 as the new starting point 610, and the tracking 600 is repeated. Once all the vessel centers 84 have been visited, the tracked paths 96' are combined to form the full vascular skeleton 96. Because the vessel center tags 84 are representative of the imaged vascular system, the system is robust. Bifurcation points, tortuous or occluded vessels, vessel overlaps, intertwined vessels, partial volume averaging, and other imaging artifacts, and vessel gaps which act alone or in various combinations to produce localized disjoints or multiplicities of the vascular path do not prevent the general tracking system 630 from tracking all vessel branches, because visitation of every vessel branch is ensured by visiting every one of the vessel tags 84.

Figure 25:
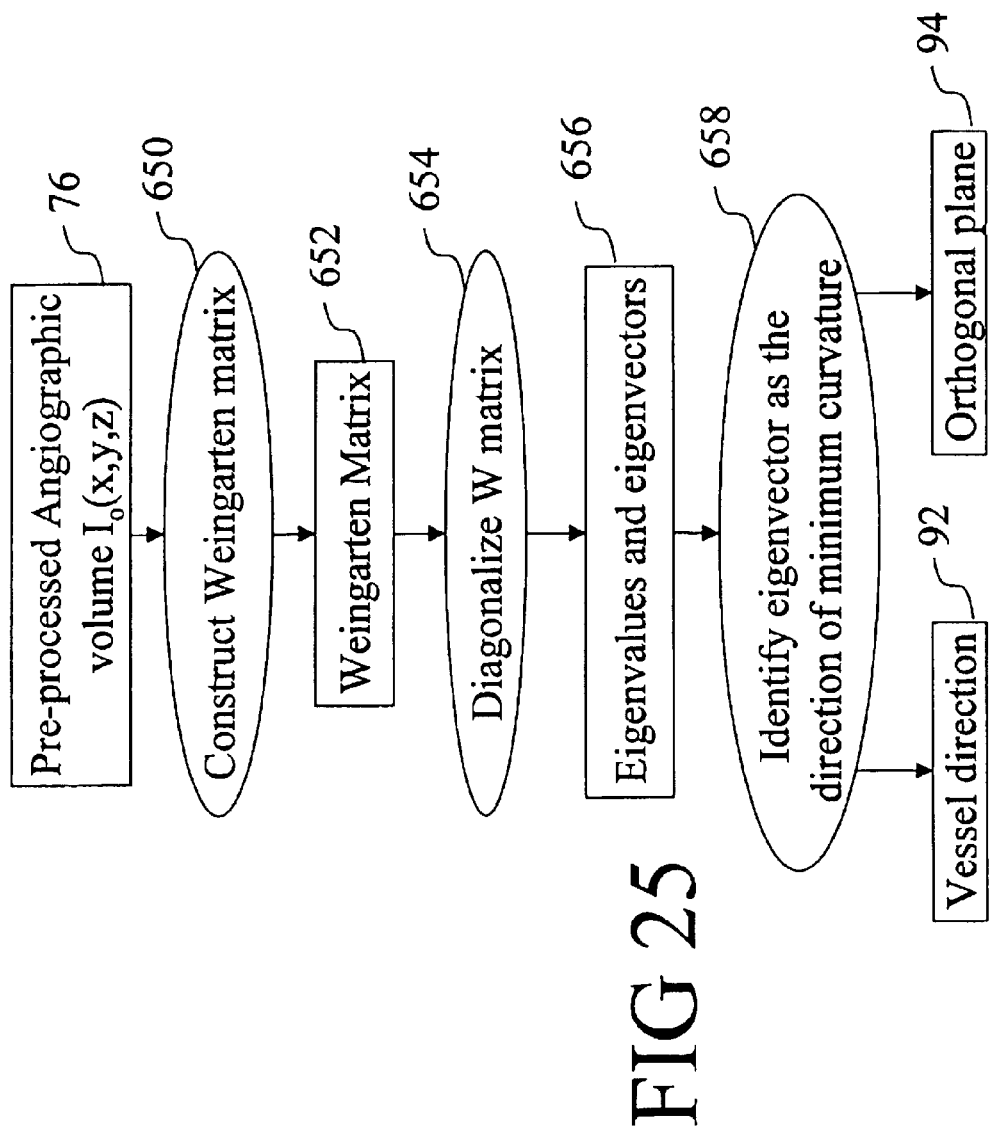
FIG. 25 shows an exemplary embodiment of the direction processor of FIG. 23.

With reference to FIG. 25, a suitable embodiment of the direction processor 90 is described. The concepts of differential geometry, curves and surfaces are preferably used for estimating the direction 92 and the orthogonal plane 94. In 2-D images, lines or curves have two directions, one direction is along the line or curve and second direction that is orthogonal to the line or curve. These directions are the vectors corresponding to the eigenvalues of the Hessian matrix at a given point. For a 2-D image, the two eigenvalues are the two curvatures at that point, i.e. the maximum curvature ($k_1$) and the minimum curvature ($k_2$). Using the differential geometry, one can represent the amplitude of the curvature and its corresponding direction by the eigenvalues and eigenvectors of the Weingarten matrix $W = F_1^{-1} F_2$, where $F_1$ is a function of the partial derivatives of the image in x and y directions, and $F_2$ is the function of the second partial derivatives in x and y directions.

The three dimensional pre-processed angiographic volume $I_o(x,y,z)$ 76 is modeled as a four-dimensional surface given by:

$$\bar{S} = \begin{bmatrix} x \\ y \\ z \\ I(x,y,z) \end{bmatrix} \quad (14)$$

where the first three elements are the spatial coordinates (x,y,z) and the fourth element is the image intensity I(x,y,z) at the voxel location (x,y,z). In this case, there are three principal curvatures. Two curvatures correspond to the two orthogonal directions in the cross-sectional plane of the tubular blood vessel, while the third principal curvature corresponds to the vessel direction or vessel orientation. The three directions can be computed using the Weingarten matrix which is a combination of the first and second form of the hypersurface, i.e. $W = F_1^{-1} F_2$, where $F_1$ is the fundamental form of hypersurface and a function of $I_x$, $I_y$ and $I_z$, the three partial derivatives of the image volume, and $F_2$ is the second fundamental form of hypersurface and is a combination of the second partial derivatives $I_{xx}$, $I_{xy}$, $I_{xz}$, $I_{yy}$, $I_{yz}$, and $I_{zz}$. More explicitly, $$W = F_1^{-1} F_2$$

where $$F_1 = \begin{bmatrix} 1 + I_x^2 & I_x I_y & I_x I_z \\ I_x I_y & 1 + I_y^2 & I_y I_z \\ I_x I_z & I_y I_z & 1 + I_z^2 \end{bmatrix}, F_2 = \begin{bmatrix} I_{xx} & I_{xy} & I_{xz} \\ I_{xy} & I_{yy} & I_{yz} \\ I_{xz} & I_{yz} & I_{zz} \end{bmatrix}. \quad (15)$$

A Weingarten (W) matrix 652 is constructed 650 according to equation (15). The eigenvectors and eigenvalues 656 of this matrix are obtained by diagonalizing 654 the Weingarten matrix, such eigenvalue decomposition being well known to those of ordinary skill in the art. The vessel direction 92 and the orthogonal plane 94 are identified 658 from the eigenvalues and eigenvectors 656 as follows. The eigenvector direction corresponding to the minimum curvature is the vessel direction 92. The plane passing though the point (x,y,z) whose normal is the vessel direction 92 is the orthogonal plane 94.

The orthogonal plane 94 is in general an oblique plane relative to the principle axes of the isotropic MRA volume 76. That is, the plane 94 is not in general parallel to one of the axial, sagittal, and coronal planes along which MRA data is typically measured. Trilinear interpolation of the MRA volume 76 is preferably performed to obtain the orthogonal plane 94 with isotropic pixels.

With reference returning to FIG. 23, the vessel segmentation processor 86 receives the orthogonal plane 94 and estimates the vessel boundaries in the orthogonal plane 94 which form part of the vessel skeleton 616.

Figure 26A:
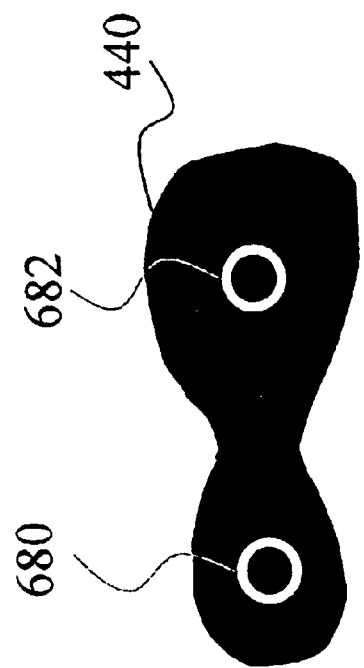
FIG. 26A schematically shows the exemplary vessel structure of FIG. 18A with initial geometric contours arranged about the vessel centers.
Figure 26B:
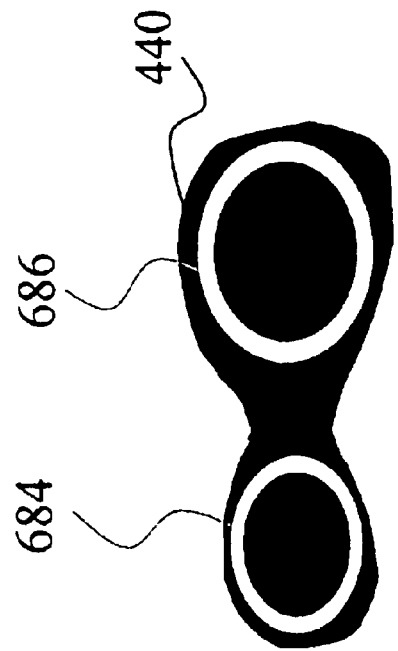
FIG. 26B schematically shows the propagating of the initial geometric contours of FIG. 26A.

With reference to FIGS. 26A and 26B, a suitable embodiment of a method for estimating the vessel boundaries is schematically described. FIGS. 26A and 26B schematically show estimation of the vessel boundaries for the flood-filled overlapping vessel structure 440 of FIG. 18A. It is known from the table of vessel centers and overlap tags 84 that there are two vessel centers 452, 454 associated with the overlapping vessel structure 440 (see FIG. 17D). Initial geometric contours 680, 682 are arranged around the vessel centers as shown in FIG. 26A. The contours 680, 682 are level set contours defined by the partial differential equation:

$$\frac{\partial \phi}{\partial t} = (\epsilon \kappa + V_p)|\nabla \phi| - V_{ext} \nabla \phi \quad (16)$$

where $\phi$ is the level set contour 680, 682, $\epsilon \kappa$, $V_p$, and $V_{ext}$ are speed functions known as the curvature, regional, and gradient speed functions, respectively, that control the propagation or flow of the contour. The level set contours 680, 682 are iteratively expanded from their initial position based on the speed functions according to equation (16), and as shown in FIG. 26B, to produces expanded level set contours 684, 686 which iteratively fill and define the vessel boundaries. The region-based level set approach has been previously used in brain tissue segmentation applications. Its application herein to vascular boundary estimation provides improved accuracy and speed. Methods previously used for vessel boundary estimation, particularly parametric contour methods, are inaccurate at sharp corners and have a tendency to bleed through gaps in the vessel structure.

Figure 27:
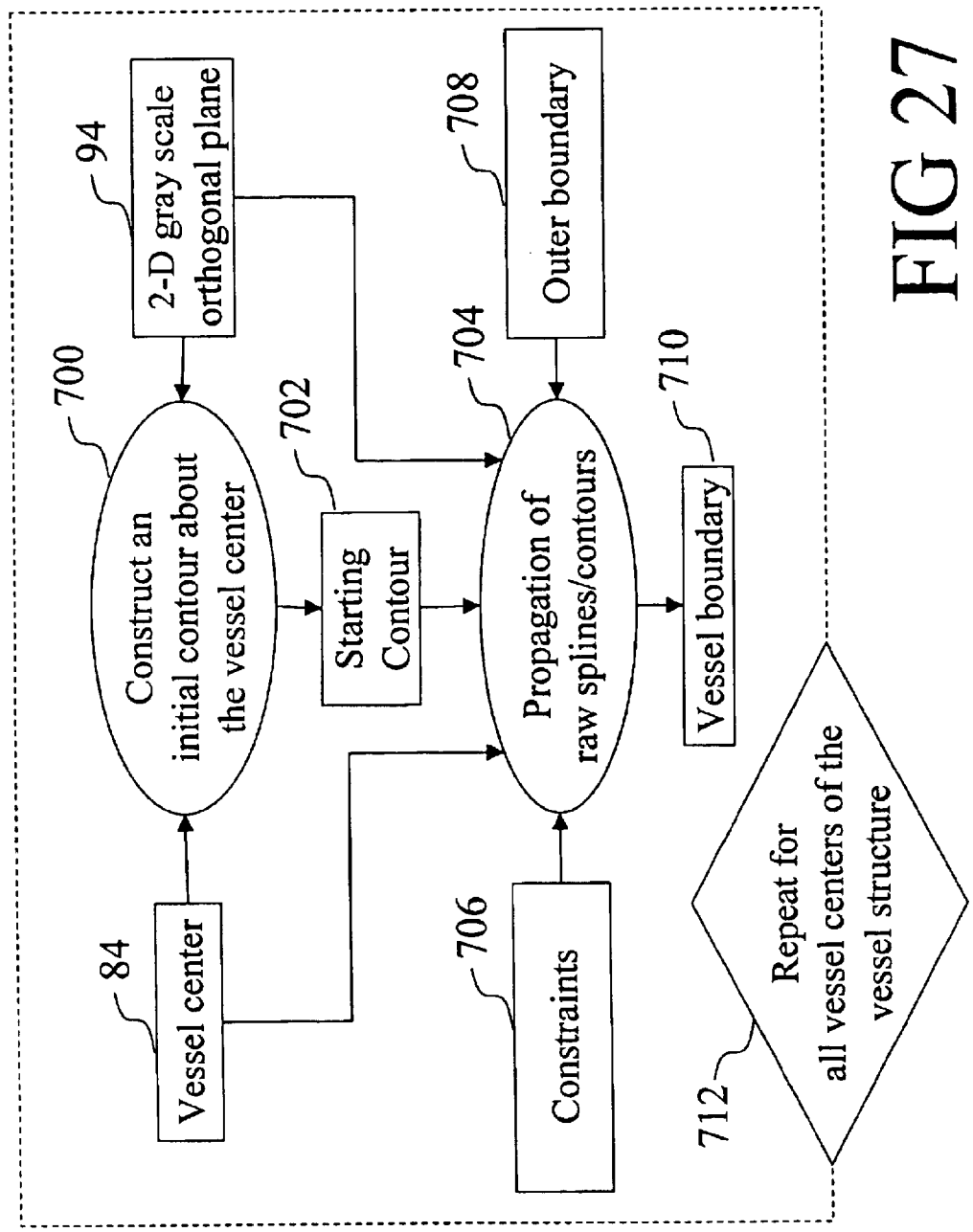
FIG. 27 shows an exemplary embodiment of the vessel boundaries contour fitting.

With reference to FIG. 27, the level set approach as applied to vascular boundary reconstruction is described. An initial contour 702 is constructed 700 about the vessel center selected from the vessel center tags 84 in the orthogonal plane 94. The vessel contour is propagated, i.e. expanded 704. The propagating 704 is iterative, occurs within the plane 94, and is constrained by appropriate constraints 706 such as the distance from the vessel center and contact between the propagating 704 contour and neighboring contours. Another constraint is the outer boundary 708 of the vessel structure in the image. These constraints serve as stopping criteria which prevent the contour from expanding too far, e.g. beyond the vessel structure or into another vessel. The final propagated contour defines the vessel boundary 710. The level set approach is repeated 712 for each vessel center of the vascular structure. For the exemplary case of the vessel structure 440 (FIG. 18A) the level set approach is repeated 712 for the two vessel centers 452, 454 as shown in FIGS. 26A and 26B.

Figure 28:
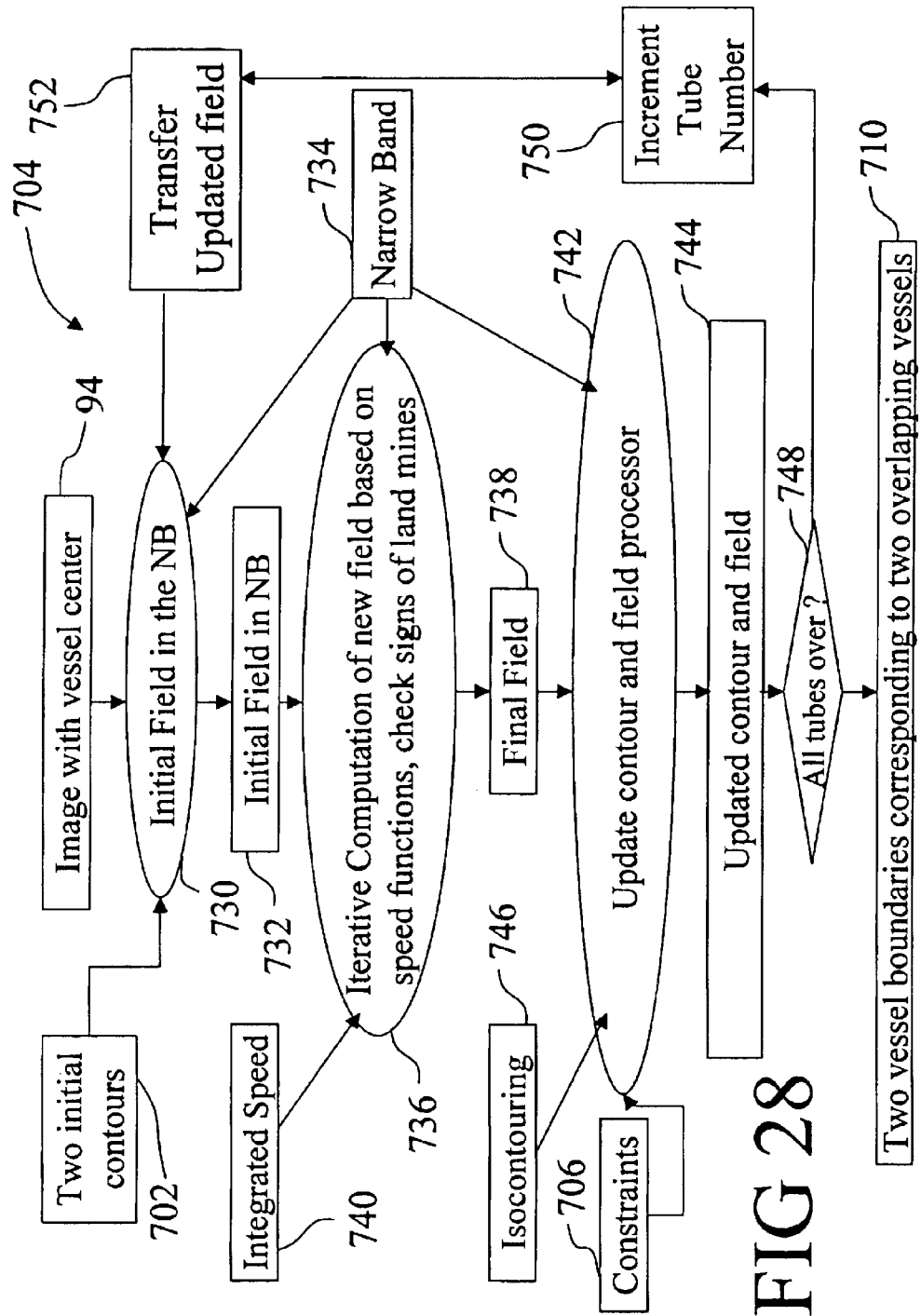
FIG. 28 shows the exemplary embodiment of the contour propagation processor of FIG. 27.

With reference to FIG. 28, a suitable embodiment of the contour propagator 704 is described. The propagator 704 of FIG. 28 is described with reference to a pair of overlapping vessels such as are shown in FIGS. 26A and 26B. Those skilled in the art can easily make the necessary changes to accommodate a vessel structure having only a single vessel center associated therewith. Thus, there are two initial contours 702, for which initial level set distance map fields 732 are computed 730 based on: the arrangement of the initial contours 702 about the vessel centers; the orientation of the orthogonal image plane 94; and the selected width of a narrow band 734 within which the level set field 732 is applied.

With continuing reference to FIG. 28, a new field 738 is calculated 736 by solving equation (16) iteratively to yield:

$$\phi_{x,y}^{n+1} = \phi_{x,y}^n - \Delta t \{V_{reg}(x,y) + V_{grad}(x,y) - V_{cur}(x,y)\} \quad (17)$$

where an integrated speed input 740 includes the three velocity terms $V_{reg}(x,y)$, $V_{grad}(x,y)$, and $V_{cur}(x,y)$. Typically, $\Delta t = 1$, i.e. each iteration corresponds to a discrete time interval. $V_{reg}(x,y)$ is a regional speed or velocity given by:

$$V_{reg}(x,y) = \max\{V_p, 0\} \nabla^+ + \min\{V_p, 0\} \nabla^-$$

where $$V_p(x, y) = \frac{\omega_R}{\gamma[1 - 2u(x, y)]}, \quad (18)$$

$\nabla^+ = [\nabla_x^+ + \nabla_y^+]^{1/2}$, $\nabla^- = [\nabla_x^- + \nabla_y^-]^{1/2}$ $V_{grad}(x,y)$ is a gradient speed or velocity given by:

$V_{grad}(x,y) = V_{grad,x}(x,y) + V_{grad,y}(x,y)$ where $V_{grad,x}(x,y) = \max\{p^n(x,y),0\}D^{-x}(x,y) + \min\{q^n(x,y),0\}D^{+x}(x,y)$ (19), $V_{grad,x}(x,y) = \max\{q^n(x,y),0\}D^{-y}(x,y) + \min\{p^n(x,y),0\}D^{+y}(x,y)$ and $V_{grad}(x,y)$ is a curvature speed or velocity given by:

$V_{cur}(x,y) = \epsilon \kappa_n(x,y)[(D^{0x}(x,y))^2 + (D^{0y}(x,y))^2]^{1/2}$ (20).

In the above equations, $\gamma$ is a damping coefficient, $u(x,y)$ is a fuzzy pixel membership function whose value lies in the range [0,1], $\omega_R$ is a regional weighting, $p^n$ and $q^n$ are the x- and y-components of the gradient strength and are calculated from the edge volume 80, $\kappa^n(x,y)$ is the curvature at location (x,y), and $\nabla_x^+, \nabla_y^+, \nabla_x^-, \nabla_y^-$ are the forward and backward level set gradients in the x and y directions which can be expressed in terms of finite difference operators of the form $D^{+/-(x,y)}(x,y)$ for forward and backward differences, and as $D^{0(x,y)}(x,y)$ for averaged differences. The regional velocity $V_{reg}$ relates to the fuzzy membership function $u(x,y)$ which for example could be computed using the fuzzy C mean algorithm known to the art. The gradient velocity $V_{grad}$ relates to the gray scale intensity gradients, and the curvature velocity $V_{cur}$ relates to the curvature in level set space.

Figure 18A:
FIG. 18A schematically shows an exemplary vessel structure corresponding to a pair of overlapping vessel centers.
Figure 18B:
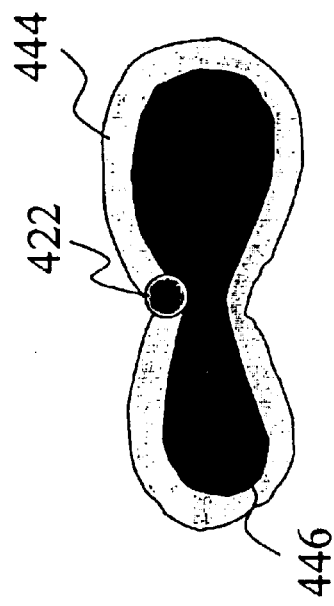
FIGS. 18B, 18C, and 18D schematically show the recursive eroding of the vessel structure of FIG. 18A.
Figure 18C:
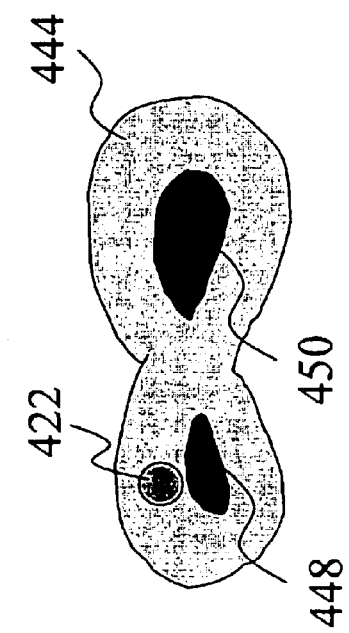
Figure 18D:
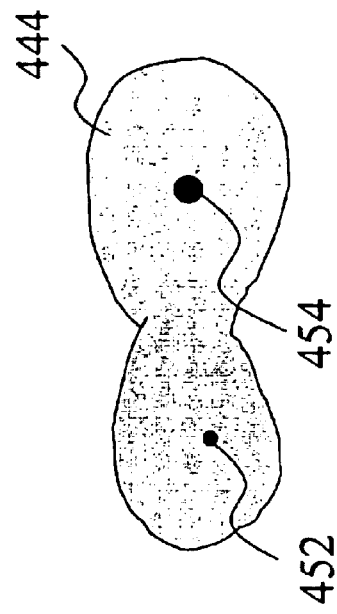

With continuing reference to FIG. 28, once the new level set field calculated according to equation (17), the contour is updated and the level set field is reinitialized 742 using isocontouring 746 in which the new contour is defined essentially corresponding to the zero contour of the level set field 738. The updating can employ the fast marching method or other techniques known to the art. The calculating 742 of the updated contour and field 744 is also constrained by selected constraints 706 as discussed previously with reference to FIG. 27. Of course, since FIG. 28 refers to an exemplary propagation of a pair of overlapping vessels such as are shown in FIGS. 26A and 26B, there are two contours 684, 686 (FIG. 26B) being calculated, one each about the vessel centers 452, 454 (FIG. 18D). Thus, an appropriate constraint in this exemplary case is that the two contours 684, 686 not overlap. Similarly, if there were three or more contours corresponding to an overlapping vessel structure, an appropriate constraint would be the non-overlapping of the three-or more contours.

With continuing reference to FIG. 28, the iterative level set propagating is repeated 748, 750, 752 a plurality of times until the contours converge to the two zero-level contours 710 corresponding to the two overlapping vessels.

Although a contour propagation employing a geometric contour in region-based level set space including a regional fuzzy membership velocity component is described herein, other methods for finding the vessel boundaries are also contemplated, such as methods using parametric contours, geometric contours employing other types of distance maps, and the like.

With reference returning to FIG. 24, the exemplary robust vessel tracking system 630 generates a full vascular skeleton segmentation 96. This extracted information can be conveyed to medical personnel in a variety of ways, including three-dimensional graphical displays, two-dimensional projections, selected vascular sub-system displays (e.g., limited to the arteriogram), and the like.

Figure 29:
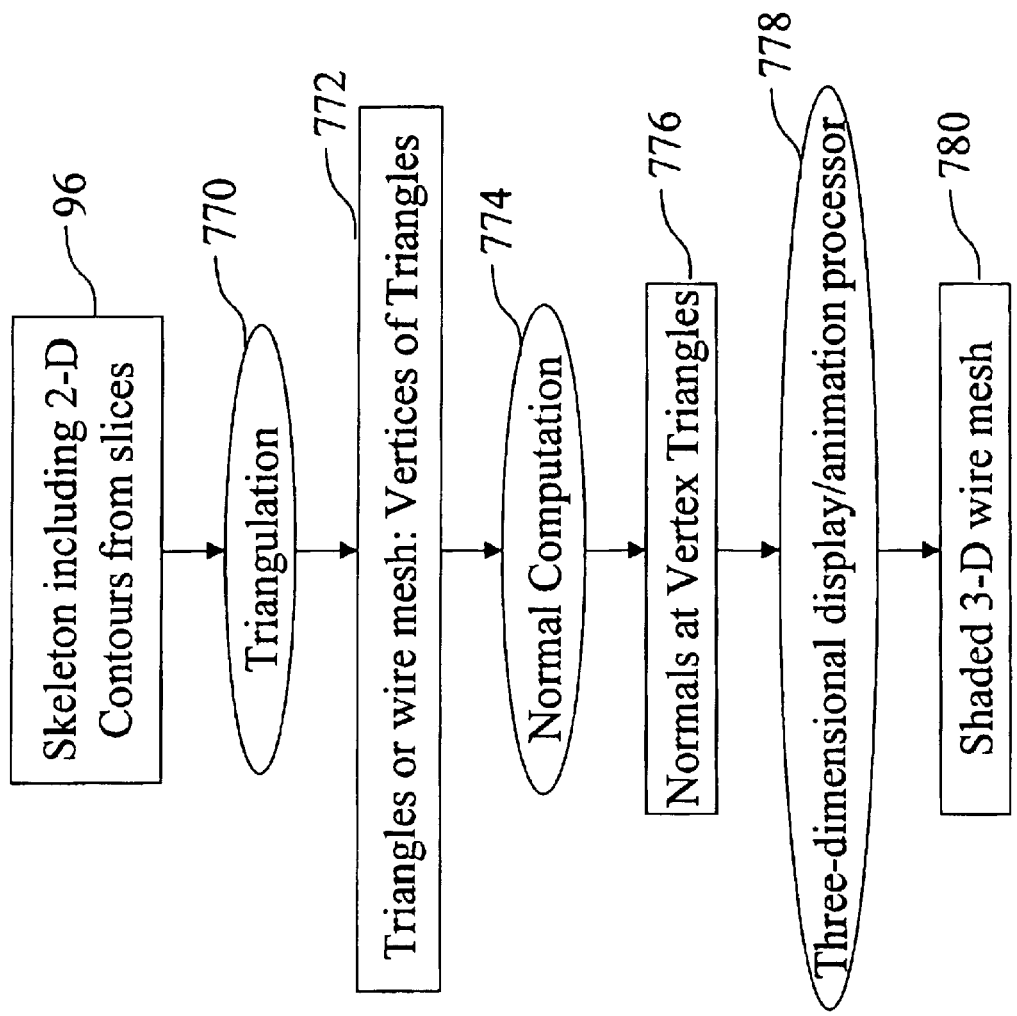
FIG. 29 shows an exemplary embodiment of a three-dimensional display processor for displaying the vascular skeleton generated by the method of FIG. 24.

With continuing reference to FIG. 24 and with further reference to FIG. 29, an exemplary embodiment of a method for generating a suitable three-dimensional display is described. The vascular skeleton 96 is supplied as an input. The tracking system 630 generates a skeleton 96 formed of a sequence of vessel contours or boundaries 710 (FIGS. 27 and 28) lying in two dimensional slices corresponding to the orthogonal planes 94 (FIG. 23). Thus, the first step is to operatively interpolate across the boundaries 710. In the exemplary embodiment of FIG. 29, shaded wire mesh method of a type known to the art is employed. A triangulation method 770 generates a three-dimensional wire mesh of triangular elements 772. The normals of the vertex triangles 776 which determine the solid vascular shape are computed 774. A display processor 778 converts the wire mesh into a shaded three-dimensional display 780. Optionally, selected graphical animation is produced 778 as well, such as graphical highlighting of a selected vascular system, e.g. the arteriogram. Of course, the three-dimensional display just described is exemplary only, and those skilled in the art will recognize that many other methods of conveying the segmented vascular tree information can also be used.

The invention has been described with reference to the preferred embodiments. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiments, the invention is now claimed to be:

1. An apparatus for producing an angiographic image representation of a subject, the apparatus comprising:
    an imaging scanner that acquires imaging data from at least a portion of a subject, the imaging data including vascular contrast;
    a reconstruction processor that reconstructs a three-dimensional image representation from the imaging data, the image representation formed of image elements and exhibiting vascular contrast; and
    a processor that converts the image representation into an edge-enhanced image representation having enhanced vascular edges and divides the edge-enhanced image representation into a plurality of two-dimensional slices formed of pixels spanning the angiographic image representation, and for each slice:
        flood-fills the vascular edges to form filled regions defined by pixels having a first value,
        identifies vessel centers through iterative removal of pixels having the first value from around the edges of the filled regions, and
    the vessel centers identified being representative of a three-dimensional vascular structure, the processor further segmenting, tracking, extracting, enhancing, or identifying information about the three-dimensional vascular structure using the identified vessel centers as operative inputs.

2. The apparatus as set forth in claim 1, wherein the converting of the image representation into an edge-enhanced imaged representation includes:
    conditional upon the vascular contrast including black blood vascular contrast, inverting the intensities of the image elements to generate an intensity-inverted image.

3. The apparatus as set forth in claim 1, further including:
a magnetic resonance contrast agent administered to the subject to improve vascular contrast.

4. The apparatus as set forth in claim 1, wherein the imaging scanner includes at least one of a magnetic resonance imaging scanner and a computed tomography scanner.

5. The apparatus as set forth in claim 1, wherein the identifying of vessel centers through iterative removal of pixels includes for each iteration:
a first erosion pass operating in a first direction across the slice using a moving window having a first shape; and
a second erosion pass operating in a second direction across the slice using a moving window having a second shape.

6. An apparatus for producing an angiographic image representation of a subject, the apparatus comprising:
an imaging scanner that acquires imaging data from at least a portion of a subject, the imaging data including vascular contrast;
a reconstruction processor that reconstructs an image representation from the imaging data, the image representation formed of image elements and exhibiting vascular contrast;
a processor that converts the image representation into an edge-enhanced image representation having enhanced vascular edges and divides the edge-enhanced image representation into at least one two-dimensional slice formed of pixels, and for each slice:
flood-fills the vascular edges to form filled regions defined by pixels having a first value,
identifies vessel centers through iterative removal of pixels having the first value from around the edges of the filled regions, and
tags vessel overlaps and vessel furcations identified as a plurality of vessel centers corresponding to a single filled region; and
segments, tracks, extracts, enhances, or identifies vascular information contained in the angiographic image using the identified vessel centers as operative inputs.

7. The apparatus as set forth in claim 6, wherein the processor connects the vessel centers and vessel edges associated therewith starting at the vessel furcations to form segmented vessel trees including vessel furcations.

8. A method for characterizing a vascular system in a three-dimensional angiographic image comprised of voxels, the method comprising:
extracting from the angiographic image a two-dimensional slice formed of pixels;
locating imaged vascular structures in the slice;
flood-filling the imaged vascular structures to form filled regions defined by pixels having a first value;
iteratively eroding the edges of the filled regions to identify vessel center points; and
repeating the extracting, locating, flood-filling, and eroding for a plurality of slices to generate a plurality of vessel center points that are representative of the vascular system.

9. The method as set forth in claim 8 wherein the locating of imaged vascular structures includes:
prior to the extracting, enhancing the vessel edges by second order spatial differentiation of the angiographic image.

10. The method as set forth in claim 8 wherein the locating of imaged vascular structures includes:
prior to the extracting, enhancing the vessel intensity contours by convolving the angiographic image with a kernel formed from a second or higher order derivative of a Gaussian function.

11. The method as set forth in claim 10 wherein the convolving of the angiographic image with a kernel includes:
decomposing the kernel into sinusoidal components; and
convolving the angiographic image with the sinusoidal components of the kernel.

12. The processor as set forth in claim 8 wherein the iterative eroding of the edges of the filled regions includes:
eroding using a process employing at least a first erosion pass in a first direction and a second erosion pass in a second direction.

13. The processor as set forth in claim 8, further comprising:
conditional upon the angiographic image being a black blood angiographic image, inverting the intensities of the image elements to generate an intensity-inverted image.

14. A processor for carrying out a method for characterizing a vascular system in a three-dimensional angiographic image comprised of voxels, the method comprising:
extracting from the angiographic image two-dimensional slices formed of pixels;
flood-filling imaged vascular structures in the slices to form filled regions defined by pixels having a first value;
eroding the edges of the filled regions to identify a plurality of vessel center points representative of the vascular system;
selecting a first vessel center point;
finding a vessel direction corresponding to the first vessel center point based on analysis of the angiographic image in the three-dimensional neighborhood of the first vessel center point;
defining a plane of the angiographic image perpendicular to the vessel direction and containing the first vessel center point;
estimating vessel boundaries corresponding to the first vessel center point in the defined plane;
repeating the selecting, finding, defining, and estimating for the plurality of vessel center points; and
interpolating the estimated vessel boundaries to produce a vascular representation.

15. The processor as set forth in claim 14 wherein the estimating of vessel boundaries includes:
defining an initial geometric contour arranged about the vessel center and lying in the defined plane; and
iteratively optimizing the geometric contour constrained to lie in the defined plane and constrained by at least one of a selected distance from a vessel center and another estimated vessel boundary.

16. The processor as set forth in claim 15 wherein the iterative optimizing of the geometric contour uses a level set framework.

17. The processor as set forth in claim 15 wherein the iterative optimizing includes:
computing a new contour based on a current contour and a fuzzy membership classification of the pixels in the neighborhood of the current contour.

18. A method for tracking a vascular system in an angiographic image, the method comprising:
identifying a plurality of vessel centers in three dimensions that are representative of the vascular system;

selecting a first vessel center;

finding a first vessel direction corresponding to the local direction of the vessel at the first vessel center;

defining a first slice that is orthogonal to the first vessel direction and includes the first vessel center;

estimating vessel boundaries in the first slice by iteratively propagating a closed geometric contour arranged about the first vessel center;

repeating the selecting, finding, defining, and estimating for the plurality of vessel centers; and interpolating the estimated vessel boundaries to form a vascular tree.

19. The method as set forth in claim 18, wherein the estimating of a vessel boundary further includes constraining the iterative propagating by at least one of:

edges of a vascular structure image containing the first vessel center;

a neighboring vessel boundary; and a pre-determined distance from the vessel center about which the geometric contour is arranged.

20. The method as set forth in claim 18, wherein the iterative propagating is computed at least in part using a fuzzy membership classification of pixels in a neighborhood of the contour.

21. The method as set forth in claim 18, wherein the finding of a first vessel direction includes:

constructing a Weingarten matrix;

obtaining a plurality of directions by implementing eigenvalue decomposition of the Weingarten matrix; and selecting the first vessel direction from the plurality of directions.

22. The method as set forth in claim 18, wherein the identifying of a plurality of vessel centers includes locating a vessel center using one of a radial line method or a center likelihood measure method.

23. The method as set forth in claim 18, wherein the identifying of a plurality of vessel centers includes locating a vessel center using a recursive erosion method.

24. The method as set forth in claim 23, wherein the recursive erosion method includes:

flood-filling each vascular structure image in the slice; and recursively eroding each flood-filled vascular structure image to identify at least one vessel center associated therewith.

25. The method as set forth in claim 23, wherein the recursive erosion method includes:

performing a first erosion pass in a first direction using a first moving window;

performing a second erosion pass in a second direction using a second moving window; and repeating the first and second erosion passes a plurality of times until the remaining at least one region is identifiable as the at least one vessel center.

26. An apparatus for characterizing a vascular system in a three-dimensional angiographic image comprised of voxels, the apparatus comprising:

a means for extracting from the angiographic image a two-dimensional slice formed of pixels;

a means for locating imaged vascular structures in the slice;

a means for flood-filling the imaged vascular structures to form filled regions defined by pixels having a first value;

a means for iteratively eroding the edges of the filled regions to identify vessel center points; and a means for generating a plurality of vessel center points that are representative of the vascular system, the means for generating being in operative communication with the means for extracting, the means for locating, the means for flood-filling, and the means for eroding.

27. The apparatus as set forth in claim 26, further comprising:

a means for estimating vascular edges associated with the plurality of vessel center points; and a means for combining the estimated vascular edges to form a vascular tree representation.

28. An apparatus for tracking a vascular system in an angiographic image, the apparatus comprising:

a means for identifying a plurality of vessel centers in three dimensions that are representative of the vascular system;

a means for selecting a first vessel center;

a means for finding a first vessel direction corresponding to the local direction of the vessel at the first vessel center;

a means for defining a first slice that is orthogonal to the first vessel direction and includes the first vessel center;

a means for estimating vessel boundaries in the first slice by iteratively propagating a closed geometric contour arranged about the first vessel center;

a means for interpolating the estimated vessel boundaries to form a vascular tree after the selecting, finding, defining, and estimating have been repeated for the plurality of vessel centers.

* * * * *